US008498819B2

(12) United States Patent
De Boer et al.

(10) Patent No.: US 8,498,819 B2
(45) Date of Patent: Jul. 30, 2013

(54) DETERMINATION OF QUALITY FEATURES IN AGRICULTURAL AND HORTICULTURAL CROPS

(75) Inventors: Anne Douwe De Boer, Dreumel (NL); Michaël Johannes Marcus Ebskamp, Nieuwegein (NL); Joost Johannes Theodorus Gierkink, Ede (NL); Ivo Laros, Renkum (NL)

(73) Assignee: Expressive Research B.V., Wageningen (NL)

( * ) Notice: Subject to any disclaimer, the term of this patent is extended or adjusted under 35 U.S.C. 154(b) by 541 days.

(21) Appl. No.: 12/527,888

(22) PCT Filed: Feb. 20, 2008

(86) PCT No.: PCT/NL2008/050097
§ 371 (c)(1),
(2), (4) Date: Dec. 3, 2009

(87) PCT Pub. No.: WO2008/103040
PCT Pub. Date: Aug. 28, 2008

(65) Prior Publication Data
US 2010/0273155 A1    Oct. 28, 2010

(30) Foreign Application Priority Data

Feb. 20, 2007    (NL) ..................................... 1033431

(51) Int. Cl.
*G01N 33/48*    (2006.01)
(52) U.S. Cl.
USPC .......................................................... 702/19
(58) Field of Classification Search
USPC .......................................................... 702/19
See application file for complete search history.

(56) References Cited

FOREIGN PATENT DOCUMENTS

WO    WO2008018790    *    6/2007

OTHER PUBLICATIONS

Bluman (Allan G. Bluman, "Elementary Statistics: A Step by Step Approach, 3rd Ed.", McGraw-Hill, Boston, MA, 1998, pp. 474-475 and 484-487).*
van Doorn et al. (Plant Molecular Biology, vol. 53, p. 845-863, 2003).*
Ling et al. (Russian Journal of Plant Physiology, 2006, vol. 53, No. 3, pp. 366-372.).*
Shi et al (The Plant Journal, vol. 2, No. 2, p. 153-159, 1992).*
Saniewski et al. (Chapter 16 Role of ABA, Gibberellens, and Auxin in Dormancy and Dormancy Release of Tulip Bulbs, In Dormancy in Plants: From Whole Plant Behavior to Cellular Control. Ed. J.D. Viemont and J. Crabbe, 2000).*
Xu et al. (Plant Growth Regul.,vol. 52, p. 1-8, Mar. 13, 2007).*
Golding et al., "Regulation of fruit ripening," Stewart Postharvest Review, 3:5 (2005) (abstract).
Crisosto, Carlos H., "Stone fruit maturity indices: a descriptive review," Postharvest News and Information, 5 (6):65N-68N (1994).
Herrera, Esteban, "Apple Orchard Management in New Mexico," New Mexico State University, <<http://cahe.nmsu.edu/pubs/_h/h-321.html>> (May 1, 2007) or <<http://aces.nmsu.edu/pubs/_h/h-321.html>> (6 pages).
Brummell, David A., "Regulation and genetic manipulation of ripening in climacteric fruit," Stewart Postharvest Review, 3:1 (2005) (abstract).
Owino et al., "Molecular basis of cell wall degredation during fruit ripening and senescene," Stewart Postharvest Review, 3:3 (2005) (abstract), also Published online at <<http:www.stewartpostharvest.com/October_2005/0wino.htm>>.
Barany et al., "Genetic disease detection and DNA amplification using cloned thermostable ligase," Proc. Natl. Acad. Sci. USA, 88:189-193 (1991).
Guatelli et al., "Isothermal, in vitro amplification of nucleic acids by a multienzyme reaction modeled after retroviral replication," Proc. Natl. Acad. Sci. USA, 87:1874-1878 (1990).
Kwoh et al., "Transcription-based amplification system and detection of amplified human immunodeficiency virus type 1 with a bead-based sandwich hybridization format," Proc. Natl. Acad. Sci. USA, 86:1173-1177 (1989).
Lizardi et al., "Exponential Amplification of Recombinant—RNA Hybridization Probes," Biotechnology, 6:1197-1202 (1988), also published online, Nature Publishing Group, at <<http:///www.nature.com/naturebiotechnology>>.
Food & Agriculture Org., CPC Ver. 2, Detailed structure and correspondences of CPC Ver. 2 subclasses to ISIC, Rev. 4 and HS 2007.
Nicot et al., "Housekeeping gene selection for real-time RT-PCR normalization in potato during biotic and abiotic stress," Journal of Experimental Botany, 56(421):2907-2914 (2005).
Altschul et al., "Basic Local Alignment Search Tool," J. Mol. Biol., 215:403-410 (1990).
Chang et al., "A simple and Efficient Method for Isolating RNA from Pine Trees," Plant Molecular Biology Reporter, 11(2):113-116 (1993).

* cited by examiner

*Primary Examiner* — Jerry Lin
(74) *Attorney, Agent, or Firm* — Hoffman & Baron LLP

(57)    ABSTRACT

The present invention relates to a method for predicting the expected value of the quality features in agricultural and horticultural product and a method for predicting the expected optimal time of harvest by comparing expression parameters at the moment prior to harvest or during the post-harvest path of genes and/or proteins related to such quality features for that agricultural and horticultural product, with (a) predetermined calibration line(s). The invention also comprises the markers M8, GAST and GDSL motif lipase and the uses thereof, as well as antibodies against them.

18 Claims, 11 Drawing Sheets

DETERMINATION OF QUALITY FEATURES IN AGRICULTURAL AND HORTICULTURAL CROPS

This application is the U.S. National Phase of, and Applicants claim priority from, International Application Number PCT/NL2008/050097 filed 20 Feb. 2008 and Netherlands Patent Application No. 1033431 filed 20 Feb. 2007, each of which are incorporated herein by reference.

BACKGROUND OF THE INVENTION

Incorporation Of Sequence Listing

Incorporated herein by reference in its entirety is the Sequence Listing for the above-identified Application. The Sequence Listing is disclosed on a computer-readable ASCII text file titled "Sequence Listing 294-364PCTUS.txt", created on May 3, 2010. The sequence.txt file is 16.3 kb byte size.

The invention relates to the determination of markers for quality features and, linked to this, determining the optimal harvest time and/or the optimal postharvest path of agricultural and horticultural products by means of molecular, biological techniques.

Determining the quality of fresh agricultural and horticultural products becomes ever more important for producers, trade and consumers. Awareness of the importance of quality increases perceptibly. Stringent requirements are set with respect to freshness, exterior features, odor and flavor of the edible product. In order to guarantee the quality as well as possible, trade has introduced so-called "tracking and tracing" systems in the production chain. In order to meet these more stringent requirements, the postharvest path is optimized. As a result, transport and storage conditions change constantly. Testing systems allowing objective determination of the quality features (quality parameters) are therefore an absolute necessity for determining quality, pronouncing expectations on future quality or improving quality.

Quality is a combination of hard (well-measurable) and soft (more difficult to measure and often apparently subjective) quality factors. Soft factors, such as extent of damage, taste, smell or aroma, condition and health and content of disorders, can sometimes be simply determined subjectively, but are often difficult to quantify. Hard factors, such as color, acidity (pH), firmness, sugar content, size or length and weight, can often be properly determined quantitatively. Some quality factors, such as dormancy status (depth of rest) or stage of development are hard only if they can be measured quantitatively on the basis of, for instance, molecular markers which are determinative of a specific stage or a specific status. Soft factors are useful only if a quantitative scale can be linked to them. This can for instance be done by making a comparison for the quality parameter with a number of references, for instance a reference for good quality which is set at 100% and a reference for poor quality which is set at 0%. A (semi)-quantitative scale for the quality value of that parameter is then obtained by determining a relative value with respect to the references. Free market processes then determine, both for soft and for hard quality parameters, what range of values is acceptable for that specific quality parameter and that specific agricultural or horticultural product.

Product quality is determined mostly by more than one quality parameter and often by a great many. It is not necessarily so that at a particular moment in time, or after a particular postharvest treatment, the values of the different quality parameters are all in the optimal range determined for that product. An optimal taste, for instance, need not go hand in hand with an optimal weight or optimal color. Often, the total product quality is a compromise of all values of the quality factors. Product quality moreover depends on the desired market or on the time of year. A product may be traded locally so that other quality factors are relevant than when the product is stored or transported. Also, the range considered optimal for a quality parameter may differ. Per quality parameter, however, a range of values can be indicated which may be considered optimal for that specific situation. These, however, are not necessarily the most optimal values in another situation, since the total product quality is determined by several quality factors. In a specific situation, a particular quality parameter can get a lower ranking in that in a particular situation another parameter is more important, so that the most optimal value for the first parameter cannot be realized at that same moment in time.

The postharvest path has a great influence on the different quality parameters. The postharvest path can be very diverse, depending on the type of agricultural or horticultural product, the location of production and/or the location of the market. It may furthermore be so that the agricultural or horticultural product is harvested during a particular time of the year while it is sold at other times during the year, therefore, the time duration of the postharvest path varies too. In the postharvest path, all kinds of storage may be involved, varying from storage at room temperature, storage at reduced temperature and sometimes even deep-freezing. Storage or keeping may involve modified/controlled atmosphere storage/packaging, inhibitors can be added, such as substances that counteract the action of certain plant hormones. All these measures and conditions in the postharvest path affect the quality parameters of the agricultural or horticultural product. Furthermore, for different cultivars of an agricultural or horticultural product, different quality parameters may be relevant or the optimal values may be different. The optimal time of harvesting an agricultural or horticultural product strongly depends on the postharvest path and the quality parameter being considered. For a specific product, the optimal harvest window (the period of time during which the harvested product yields the most optimal values for a particular quality parameter) in relation to a quality parameter therefore depends on the postharvest path that will be chosen and the criteria set by the market. So, looking at total product quality or at a specific quality parameter, there is no such thing as an optimal harvest window for all situations. The optimal harvest window should therefore be determined from one situation to the next and also from one product (cultivar or variety) to the next (cultivar or variety). For quality control it is therefore vital that the most important quality parameters after the postharvest path can be predicted at the time of harvest or during the postharvest path. Then, on the basis of this prediction, it can be determined what is the optimal harvest window for a specific agricultural or horticultural product at a given time for a given situation.

For the specific product fruit, two types of fruit ripening are distinguished: fruit that ripens under the hormone ethylene produced by the plant itself (climacteric fruit) and fruit that is more or less independent of this (non-climacteric fruit). From recent studies, however, it appears that this division is arbitrary because some fruit types or varieties do not meet this classification and take an intermediate form (Golding et al., 2005, *Stewart Postharvest Review* 3:5). During ripening, the climacteric types of fruit have a moment at which the production of ethylene actually begins. The moment just prior to this, the preclimacteric, is physiologically speaking the optimal moment of picking. However, this moment does not necessarily coincide with the optimal moment for commercial quality parameters such as, for instance, size of the fruit, desired sweetness and color. If for these commercial reasons a later moment of picking is preferred, this has direct consequences for keeping quality and keeping duration. In the case of non-climacteric fruit, the moment of picking is presently determined by mainly commercial quality parameters.

After fruit picking, it generally takes some time before the fruit is ripe for sale, i.e., can be consumed by the consumer. A large part of this time is required for transport to a location where the fruit is processed (e.g. packaged) and for transport from that location to the locations of sale, for instance the auction hall, and from there to the retail trader. This is especially the case if the fruit is to be transported from one continent to another, for instance in the case of tropical fruits. During this time, however, the ripening process continues, and it often happens that either the fruit when ready to be sold is overripe or, conversely, it is not yet ripe enough to be sold. In the first case the fruit is unsalable or can be sold only at a lower price, in the second case the fruit is to be stored until it has ripened sufficiently. In both cases, therefore, economic losses are suffered. The postharvest path also greatly influences the development of negative quality features, for instance disorders such as "hollow and brown" or "weak necks" in some pear cultivars.

The proper harvest time will therefore depend on the commercial parameters and the required postharvest time required for processing and transporting the fruit. However, the condition of the plant (size, affection by disease) and the climatologic conditions during the development of the fruit (temperature, amount of sunlight), or the conditions of cultivation (for instance extent of fertilization) are determinative both of the physiological and of the commercial parameters. Therefore, an optimal harvest time applicable to all situations can never be given. In addition, determining the optimal harvest time is of great importance for the grower in connection with the planning and deployment of personnel. Since in some cases not the postharvest path but the previous history of the fruit is responsible for the development of disorders during or after storage, it is of great importance to be able to measure those parameters objectively.

Ripening of fruit is determined by the breakdown of chlorophyll and the accumulation of pigments, softening through changes in texture mainly due to breakdown of cell walls, changes in the accumulation of different sugars and organic acids, of which the latter mainly determine the taste, and production of volatile substances that provide the aroma. A fruit is assessed to be "ripe" if it is at the stage where it has reached a sufficient development, so that after harvest and subsequent treatment, the quality is at least minimally acceptable for the eventual consumer (Reid, M. S., 1992, In: Peaches, Plums and Nectarines: Growing and Handling for Fresh Market, LaRue, J. H. and Johnson, R. S. (eds.), Univ. Calif. Dept. Agricult. Nat. Resourc. Publ. No. 3331, 21-28). To determine this moment and/or to pronounce on the expected quality, a suitable maturity index is being sought. Over the years, different, often external features of fruit have been proposed to serve as such. Crisoto describes, for stone fruit, the use of the parameters "size and shape", "hardness of the flesh", "concentration of soluble solids", "acidity" and "color" (Crisoto, C. H., 1994, Postharvest News and Inf., 5(6):65N-68N). For apples, Herrera mentions the features "basic color", "pickability" 'hardness of the flesh", "concentration of soluble solids", "starch content", "number of days from blossoming", "redness" and "color of the seeds" (Herrera E., 1998. However, in practice, such methods prove not to be properly usable because the respective maturity index is not accurate enough or the index has hardly any predictive value with respect to expected quality for particular fruit types or varieties.

Of the specific product tulip (*Tulipa gesneriana*), the bulbs are lifted in the Netherlands in spring at the time when the depth of dormancy is considered optimal. If harvesting is unduly delayed, the soil will become unduly wet (through rain), so that the risk of fungi increases strongly and the machines cannot be fielded anymore. It is very important to determine precisely what the depth of dormancy is at the time of harvest. The harvest window is determined by the moment when dormancy is maximal and actually has only an end depending on the weather conditions. The quality parameter that is to be determined at the time of harvest in this case is the depth of dormancy. Optimal dormancy ensures a specific bulb size so that maximum length and thickness of the flower stem can be obtained after the postharvest path. After the depth of dormancy has become maximal, the size of the bulb no longer changes. The quality parameter length and thickness of the flower stem depends on the depth of dormancy at harvest time; the optimal moment and, associated therewith, the best possible values for quality is achieved if the depth of dormancy is maximal. At present, the moment of browning of the fleece on the outside of the bulb is used as indicator that the depth of dormancy is maximal, but in many cases this appears to be unreliable. A good molecular marker with which the value of the quality parameter length and width of the flower stem correlates and from which, consequently, the depth of dormancy can be derived, is very important here. In this case, the postharvest path for tulip bulbs consists in storage at higher temperature until the growing point in the bulb has shifted from the vegetative phase to the generative phase. Then, the bulbs are stored at lower temperature until the cold-dependent break of dormancy has been reached completely. Finally, planting of the bulb in potting soil and growth (stretching of the flower stem followed by flowering) takes place.

Molecular tests are also desired for determining when the bulb has sustained sufficient cold to break dormancy. This is the moment when planting can take place. Insufficient break of dormancy through too short a cold period also yields a poorer quality. The quality parameter of the maximum length the flower stem can reach is important here too. Here too, a shorter cold period once more results in a lesser length of the flower stem. The quality parameter to be determined in the final path of postharvest is the extent of dormancy break. The eventual quality parameter of maximum length (and thickness) of the flower stem in tulip is therefore dependent on several quality parameters during the postharvest path, the first being the depth of dormancy during harvest, then the complete transition of the growing point in the bulb from vegetative to generative and finally the complete break of dormancy through a period of reduced temperature. Comparable problems for which molecular markers are required occur in other bulbous and tuberous crops, such as lilies, daffodils, hyacinths, freesias, onions, garlic and amaryllis.

For the specific product cut flowers, the harvesting moment with respect to bud ripening is of importance for determining the important quality parameter "length of vase life". Molecular markers during harvest, and especially markers involved in the aging of the flower and whose extent of gene expression or protein concentration correlates with the length of the vase life, are good candidates for use in a test for the expected length of vase life. During the postharvest path, the degree of stress influences the length of vase life. For almost all cut flowers, including tulip, rose, alstroemeria, iris, lily, Dendranthema (chrysanthemum), gerbera, carnation, freesia, Cymbidium, and Gypsophila, it is important to predict an expectation of the vase life with molecular markers.

For the specific product pot plant or patio plant, stress has a direct influence on the level of the process of leaf aging. Leaf aging is directly related to the degree of leaf yellowing. In the case of pot plants, most often, harvesting is not the same as harvesting for instance fruits, unless this happens through striking of cuttings, but harvesting is characterized by the removal of the plant from, for instance, the greenhouse and transport to, for instance, the auction. For almost all pot and patio plants, including Pelargonium, Petunia, Dendranthema (chrysanthemum), Ficus, kalanchoë, Dracaena, Phalaenopsis, Hedera, Begonia, Spathiphyllum, Hydrangea and Euphorbia, it is of importance to measure the (stress related) quality with the aid of molecular markers.

For the specific product cucumber, the ripening phase and stress both have a negative effect on the quality of the cucumber. One of the (negative) quality factors for cucumber is yellowing of the cucumber. For other vegetable crops too, such an expectation of the quality is of very great importance, for instance for lettuce, endive, leek, types of cabbage such as broccoli, cauliflower, Chinese cabbage, red cabbage and other types of cabbage, and chicory. For vegetable crops that are sold in pre-cut form, pre-packaged or not pre-packaged, it is also of importance, after cutting, to measure the effect of stress on aging via molecular markers to thereby monitor the quality of the cut product.

For the specific product grape, the composition of the substances produced in the grape at a particular time is of great importance for the quality of the product (wine, port wine, champagne and the like). The quality parameter of taste of, for instance, port wine can be quantified via, for instance, a taste panel. Correlation of taste with the level of molecular markers at the moment of harvesting, or during the postharvest path, is important to recognize the quality of the end product already at an early stage. This also holds for other crops, such as herbs and spices, specific types of berries, for instance olives and juniper berries, and other agricultural or horticultural products where the presence of taste-determinative components can be determined via molecular markers so that the taste quality of the eventual product can be predicted.

Molecular biological techniques such as genome and transcriptome analysis have been used on a large scale in recent years to investigate all kinds of processes that play a role in product quality. For instance processes involved in the ripening of fruit have been further investigated and efforts have been made to identify the enzymes playing a role in them (see inter alia Golding J. B. et al., 2005, Brummell, D. A., 2005, and Owino, W. O. et al., 2005, all in: Stewart Postharvest Review 3:5). The results discussed in the above-mentioned review papers have been used mainly for influencing the different processes, among which the ripening process, for instance by making transgenic plants with overexpression or blocked expression of certain genes that code for enzymes allegedly playing a role in the process. However, until now, molecular biological techniques have not yet been used for predicting the expected value of a quality parameter or for determining the optimal harvest window for a given situation.

The invention relates to a method needed to identify and isolate molecular markers, genes or proteins, for which the value of the gene activity or the protein concentration, respectively, at a particular moment during harvest or during the postharvest path correlates with a specific quality parameter at a specific moment, and the method for predicting after measurement of the value of this marker during the harvest or during the postharvest path the value of the quality parameter during the harvest, the postharvest path or at the end of the postharvest path, or the expectation for a specific situation.

DETAILED DESCRIPTION OF THE INVENTION

Figure 1:
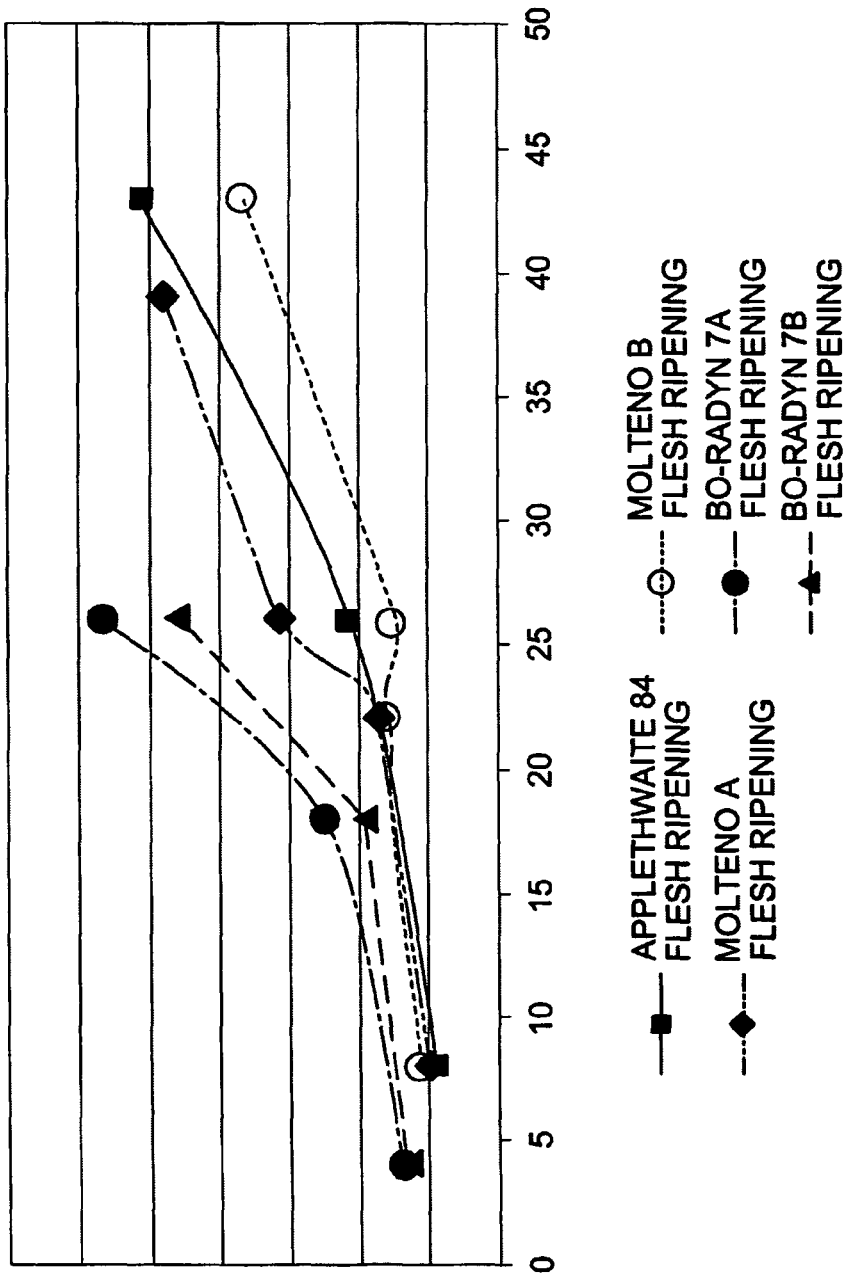
FIG. 1. Course of ripening over time with pear cv. Bon Chretien in five orchards. In the diagram, an average value for the totality of the used markers (βxyl, PG and peroxidase 424/87) is plotted against time in days.

In the following, the invention is explained in detail for determination of the expectation (or prediction) of the ripening and/or the moment of harvest of fruit, in particular apple and pear. Naturally, the general technology is also useful for determining markers for quality features and, linked to this, determining the optimal time of harvesting of agricultural and horticultural products other than fruit.

Ripening of fruit is a process whereby chlorophyll is degraded and pigments start forming, while the fruit loses its hardness, whereby sugars are formed and organic acids, and whereby volatile aromatic substances are formed. These activities necessitate certain biochemical processes in the cells of the fruit being switched on or switched off. One of the most studied changes in the metabolism is the production and the effects of ethylene, which plays a part mainly in climacteric fruit (for instance tomato, melon, apple, avocado, kiwi and banana). In these fruits, ethylene is a prerequisite for ripening because it acts like a hormone that can activate transcription factors which, in turn, influence gene expression in the cell (so-called ethylene signaling route).

It appears inter alia from the present invention, however, that inter alia genes involved in the texture of the fruit could, in principle, be a suitable parameter for determining the expectation of the ripeness and the proper picking time for fruit. From the above-cited literature, however, and from the Examples presented hereinbelow, it can be concluded that it is preferred to examine several ripening indices during ripening of the fruit. Genes that are involved in changes in hardness of the fruit and which are eligible for investigation are inter alia: β-xylosidase (βxyl), polygalacturonidase I and II (PGI and PGII), putative cell wall peroxidase 424/87 (87), Xyloglucan endotransglycosylase (XET), actin marker M8, expansin and glucanases such as endo-β-1,4-glucanase, NADP-dependent D-sorbitol-6-phosphate dehydrogenase and/or alpha amylase.

The essence of the invention is first to develop a calibration line for each variety, whereby the expression of the above-mentioned genes (with respect to the ripeness of fruit) or other genes (with respect to other quality parameters mentioned hereinabove) is followed over the course of the ripening process. It can be determined here which of the above-mentioned genes have the best correlation with a quality feature after this path, in other words, which genes will be best determinative of the expectation with respect to the value of this quality feature. It appears that during ripening—in any case with some of the tested fruit varieties—as shown in the Examples, at a given moment, different genes yield the best correlation with, in this case, the quality feature hardness.

Determining Expression Profiles of Genes and Proteins.

To obtain reliable results and tests it is important that sampling be done in a reproducible manner. Herein, "determining an expression profile" of genes is used as is customary in the field of technology and relates to a method for measuring the transcriptional status (mRNA) or the translational status (protein) of one or more genes in a cell. For mRNA and protein isolation from plants, available standard protocols can be used. In a number of cases, these will require small modifications if the tissue has a very thick cell wall or contains very many sugars. These protocols and modifications are part of the skilled person's knowledge. Depending on the method used, such measurements can entail a genome-wide determination of expression, but also the measurement of only the expression profile of a few genes, which results in the realization of a "gene expression profile" or an "expression profile", which terms will be used as such in the following. An "expression profile" comprises one or more values that relate to a measurement of the relative presence of a gene expression product. Such values comprise measurements of RNA levels or protein concentrations. Therefore, the expression profile can comprise values that represent the measurement of the transcriptional status or the translational status of the gene. With respect to this, reference is made to U.S. Pat. Nos. 6,040,138, 5,800,992, 6,020,135, 6,344,316 and 6,033,860.

The transcriptional status of a sample comprises the identity and the relative occurrence of the RNAs, in particular mRNAs, present in the sample. Preferably, a sufficient number of genes are measured for determining the transcriptional status of the sample. The transcriptional status can also be suitably determined by measuring the presence of transcript via any of the existing gene expression technologies.

The translational status comprises the identity and the relative occurrence of the constituent proteins in the sample. Here too, a number of proteins sufficient for determining the translational status of the sample will suffice. As is known to those skilled in the art, the transcriptional status and the translational status are often correlated. Each value in the expression profiles, as determined and measured in the present invention, is a measurement that represents the absolute or relative expression of a gene. The expression levels of these genes can be determined via any method known in the field for determining the level of an RNA or a protein in a sample. First, the expression profiles of a large number of genes are to be analyzed. Techniques that can be used to this end are direct sequencing: such as transcriptome sequencing (Roche & 454 Sequencing); digital profiles with Clonal Single Molecule Array™ (i.e., sequencing technology) (Solexa); electronic Northern is used for calculating gene expression levels in different samples, and is based on the number of sequences for a specific gene that are identified in a set of cDNA libraries. Variations thereon are Serial Analysis of Gene Expression (SAGE), Tandem Array Ligation of Expressed Sequence Tags (TALEST) and cDNA AFLP (amplified fragment length polymorphism), which all enable detection of differentially expressed transcripts.

In addition, there are techniques for determining the presence of transcripts with hybridization, such as micro-arrays. Such a micro-array can be a DNA array, an oligonucleotide array or, in general terms, a nucleic acid array. The skilled person will be able to obtain self-designed arrays and associated array reading equipment from specialized suppliers (for instance Affymetric Corp., Santa Clara, Calif., USA).

For monitoring a smaller number of transcripts, use can be made of: Northern analysis, this is one of the standard techniques for detection and quantification of mRNA levels. With this technique, the size of the mRNA and any alternative splicing and multigene families can be detected. With reverse transcription polymerase chain reaction (RT-PCR) analysis, mRNA molecules can be detected with high sensitivity because exponential amplification of the transcripts takes place, this technique is also called quantitative PCR. This technique is particularly suitable for highly accurate quantification of mRNA transcripts. Since with this technique very large numbers of samples can be analyzed, and this technique can also be automated (Applied Biosystems 7900HT system Foster City, USA), it is at present preferred for analyzing transcripts. In addition, other technology platforms can also be used, such as the PAMChip® (i.e., instrument for parallel analysis of biomaterials in the nature of microarray apparatus) (Pamgene, Den Bosch, the Netherlands) or the BioTrove OpenArray™ technology (i.e., RT-PCR instrument) (BioTrove Inc., Woburn, USA). The knowledge of the operation of the respective platforms can also be supplied by the manufacturer in case the skilled person is unfamiliar with a specific platform.

In these technologies, the presence of a particular marker gene is determined by selective amplification of this gene. This is generally done with the aid of primers. In general, the term "primers" refers to DNA strands that can start the synthesis of DNA. DNA polymerase cannot de novo synthesize DNA without primers: it can only lengthen an existing DNA strand in a reaction in which the complementary strand is used as template for dictating the sequential order of the nucleotide chain to be composed. Primers serve for providing the DNA polymerase with a starting point for the amplification reaction. Consequently, primers are generally short nucleotide chains (oligonucleotides) with a length of approximately 10 to approximately 50 nucleotides. These primers are complementary to the gene sequence to be amplified and will therefore, presented in single-strand form to single-strand DNA or RNA, form duplex nucleotide chains with the target sequence by hybridization. Ideally, for hybridization, exactly complementary nucleotide chains are required, but it appears that a sufficient hybridization is also effected if not all nucleotides are complementary, so-called 'mismatches'. In addition to the extent of complementarity, the capacity of primers to hybridize with the target sequence has also to do with the reaction conditions in which the hybridization takes place.

DNA amplification: the term DNA amplification will be used to indicate the in vitro synthesis of double-strand DNA molecules with the aid of PCR or a comparable amplification system. The amplifications required for the present invention can utilize a variety of amplification methods, such as the Polymerase Chain Reaction (PCR; Mullis 1987, U.S. Pat. Nos. 4,683,195, 4,683,202 and 4,800,159) or the Ligase Chain Reaction (LCR; Barany 1991, Proc. Natl. Acad. Sci. USA 88:189-193; EP Appl. No. 320,308), Self-Sustained Sequence Replication (3SR; Guatelli et al., 1990, Proc. Natl. Acad. Sci. USA 87:1874-1878), Strand Displacement Amplification (SDA; U.S. Pat. Nos. 5,270,184, and 5,455,166), Transcriptional Amplification System (TAS; Kwoh et al., Proc. Natl. Acad. Sci. USA 86:1173-1177), Q-Beta Replicase (Lizardi et al., 1988, Bio/Technology 6:1197), Rolling Circle Amplification (RCA; U.S. Pat. No. 5,871,921), Nucleic Acid Sequence Based Amplification (NASBA), Cleavase Fragment Length Polymorphism (U.S. Pat. No. 5,719,028), Isothermal and Chimeric Primer-initiated Amplification of Nucleic Acid (ICAN), Ramification-extension Amplification Method (RAM; U.S. Pat. Nos. 5,719,028 and 5,942,391) or other suitable methods for the amplification of DNA. For amplifying DNA with a small number of mismatches with respect to the amplification primers, an amplification reaction can be carried out under conditions of reduced stringency (in other words, a PCR reaction using an annealing temperature of 38° C., or in the presence of 3.5 mM MgCl2). The skilled person will be able to select the proper stringency conditions.

That a small number of mismatches in the primers are allowed means that a primer for a particular target sequence can be usable in determinations in several types of organisms. This is because different organisms, in particular different species and even different varieties within one species, often exhibit differences in the amino acid sequences of their proteins and/or in the nucleotide sequences of the genes that code for these proteins. By presently allowing small differences, one and the same primer can be used for the determination in several organisms. In the Examples, it is shown, for instance, that the primers are eminently suitable for determining marker genes and/or 'house-keeping genes' in different varieties within one species (for instance apple) and even for different species (apple and pear).

Relative transcription levels are calculated in relation to suitable controls, which are present in the sample. Such controls are for instance constitutively expressed genes, such as, for instance, particular 'house-keeping' enzymes. Particularly preferred are the constitutive markers phosphoglycerate kinase (PGK, EC 2.7.2.3) or elongation factor 1α (eF1α), see also the Examples.

In addition, expression profiles can be determined on the basis of protein profiles. Here too, initially, for detection, techniques will be used with which very many protein profiles can be examined simultaneously. An example thereof is gel electrophoresis. Here, proteins are first separated on the basis of their molecular weight. Optionally, after this, a second separation can take place for a second dimension (2D) based on the isoelectric point of the proteins (pH gradient). Thereupon, the amino acid sequence of differentially expressed proteins can be determined with the aid of mass spectrography. Another technique for examining many proteins simultaneously is the use of the so-called protein arrays (Ciphergen Biosystems, Fremont, Calif., USA), whereby the amount of a great many different proteins and protein peptides can be quantified. Here too, with the aid of mass spectography, the amino acid sequence of the proteins can be determined. In this embodiment, the values in the expression profile are obtained by measuring the concentration of the protein products of the marker genes. The concentration of these protein products can be determined through the use of, for instance, specific antibodies for these protein products. The term "antibody", as used herein, relates to an immunoglobulin molecule or immunologically active part thereof, i.e. an antigen-binding part. Examples of immunologically active parts of immunoglobulin molecules are, for instance, F(ab) and F(ab')2 fragments, which can be generated by treating the antibody with an enzyme such as pepsin. The antibody can be a polyclonal, monoclonal, recombinant and for instance a chimeric or "single-chain" antibody. Detection of the gene product is facilitated by coupling the antibody to a detectable substance (i.e. labeling the antibody). Examples of detectable substances are inter alia various enzymes, prosthetic groups, fluorescent materials, luminescent materials, bioluminescent materials and radioactive materials. Examples of suitable enzymes are inter alia horseradish peroxidase, alkaline phosphatase, β-galactosidase and acetyl choline esterase; examples of suitable prosthetic groups are inter alia streptavidin, or avidin and biotin; examples of suitable fluorescent materials are inter alia umbelliferone, fluorescein, fluorescein isothiocyanate, rhodamine, dichlorotriazinylamine fluorescein, dansylchloride and phycoerythrin; an example of a luminescent material is inter alia luminol; examples of bioluminescent materials are inter alia luciferase, luciferin and aequorin; and examples of suitable radioactive materials are inter alia $^{125}$I, $^{131}$I, $^{35}$S and $^{3}$H.

Currently, the detection of proteins mostly takes place with the aid of antibodies and to this end, different detection systems are available such as lateral flow assays, but also detection equipment that utilizes chemoluminescence such as the GeneGnome (Syngene, Cambridge, United Kingdom). It is also possible to measure the direct interaction between antibody and protein with, for instance, the Biacore™ (i.e., compositions for measuring molecular interactions) (Biacore AB Corp., Uppsala, Sweden) or the IBIS iSPR (IBIS technologies, Hengelo, the Netherlands) or paramagnetic particles (European Pat. Applic. No. 20040744572). Depending on the number of protein markers, the best detection platform can be selected by the skilled person. The knowledge about the operation of the respective platforms can also be supplied by the manufacturer if the skilled person is unfamiliar with a specific platform.

In principle, for any quality feature that can be objectively determined, a calibration line can be made on which the expression of markers (mRNA or protein) can be plotted against the quality feature. This can be done prior to, during or after harvest. On the basis of the correlation of the markers with the feature, it is determined for a particular period of time which marker(s) correlates most (and hence is most reliable as a predictor). Quality features that may be considered are, for instance: hardness of fruit, dormancy break in bulbous crops and vase life in cut flowers and other parameters mentioned in the introduction. It is of course important to keep the conditions before and after harvest as equal as possible to the conditions as will be used later. It will be understood, for instance, that a calibration line made with storage of fruit at 4° C. will not be the same as the calibration line of fruit stored at 20° C. or room temperature. A calibration line made at 4° C., however, can be used for predicting the expected ripening of fruit at other temperatures because the measured expression indicates the extent of ripening. Inaccuracy is then caused in that it cannot be derived from the calibration line for how long storage under those other conditions is still needed (because the speed of ripening is different). A calibration line that is specific for a particular situation is therefore preferred. The calibration line should further indicate when it is expected that a product will meet a given quality criterion. This may mean, for instance, that he markers give an expectation about the period of time that fruit can be stored in cooled condition, or for how long the bulbs will still need cold before their dormancy is broken. It is naturally important, when the samples are not yet in a controlled environment, to sample regularly and to determine the expression profile to adjust and optimize the expectation. For it may be that the samples develop faster or, conversely, slower, on the basis of the conditions. In fact, a calibration line based on the new situation would become steeper or flatter. It will be understood that a calibration line made on the basis of a fruit ripening during a hot, dry summer will not give an accurate prediction on the expected duration of ripening in a cool, wet summer. However, because—as already mentioned in connection with the variations in the conditions of storage—the measured expression values do indicate the ripeness condition of the fruit, it can yet be determined on the basis of a comparison with the calibration line whether the fruit is ripe to be picked. As appears also from the Examples, for particular quality features, already calibration lines have been made.

In cut flowers, via a combination of a marker for flower senescence and a marker for the degree of stress, which both correlate with the length of vase life during the postharvest path, the length of vase life can be predicted. To this end, a cysteine protease and a GDSL-motif lipase can be used.

As indicated hereinabove, with pot plants, yellowing of leaves is an important quality parameter. During the harvest, or during the postharvest path, this negative quality parameter (which depends directly on the age of the leaf) can be predicted by markers involved in the process of leaf aging, which correlate with the extent of leaf yellowing, optionally in combination with markers with a higher expression in older leaves than in younger leaves and which correlate with the extent of leaf yellowing. The quality parameter of "yellowing" in cucumber can be predicted in a manner comparable to that with pot plants by molecular markers during the harvest or during the postharvest path.

Similarly, with grapes, if the taste can be given a quality value that is reproducible, the taste can be predicted during the harvest or the postharvest path by using a combination of markers involved in the biosynthesis of taste components and whose gene expression correlates with the degree of taste.

In addition to being applicable to the kinds of fruit mentioned in the Examples, the present invention of determining markers of the ripeness and time of harvest and predicting the expected quality features is also applicable to all kinds of fruit for which the time of harvest and the duration of after-ripening are important factors for the consumability and the economic conditions regarding the making available of the fruit (transport, storage). In addition to being used for apple and pear, the invention may therefore be suitably used for the following kinds of fruit: citrus fruits such as orange, mandarin, lemon and minneola, melon, tomato, peach, plum, grape, currant, gooseberry, blackberry, raspberry, cherry, pineapple, mango, kiwi, litchi, banana, paprika, and avocado, including all varieties and cultivars thereof.

In addition, the invention is applicable to all agricultural or horticultural crops whose quality is for a large part determined by the time of harvest and the postharvest path. Examples of crops that meet this criterion are the cut flowers, ornamental pot plants, bulbous plants and cucumbers already mentioned in the introduction, but further also virtually all other kinds of vegetables and grain, such as, for instance, lettuce, tomato, potato, alfalfa, asparagus, tapioca, yam, all kinds of cabbage (cauliflower, curly kale, Brussels sprouts, savoy cabbage, conical cabbage, and the like), chicory, (baby) carrots, winter carrot, pulses, wheat, maize, rice, oats, barley and plants which are used as herb, e.g. pepper, dill, chervil, rosemary, and so forth. Also, the invention is applicable to crops that are not consumed as such but are used for the production of commercially important products, such as, for instance, fruits of the oil palm, olives, sugarcane, sugar beet, sunflowers, soybeans, coffee beans, cocoa beans, wood-producing plants, and all crops as mentioned on the website of the Food and Agriculture Organization (FAO) of the United Nations.

Practical Application of Testing Markers in Samples.

Markers can be tested in an application lab (off-site) or on site in a simple (lab) environment.

In sending samples to an application lab, various possibilities exist. A first possibility is for the samples to be brought fully intact to the application lab. This can be done, for instance, with (intact) fruit. As long as the transport conditions are not extreme (temperature differences, pressure on samples, etc.), transport will not affect the outcome of the tests. Upon arrival at the application lab, the samples need to be fixed as soon as possible, for instance by freezing in liquid nitrogen, or processed immediately for further analysis. In case of large numbers of samples, sampling, extraction and detection may be robotized.

The second possibility is testing samples in situ. The number of steps and the complexity of the operations will have to be limited to allow the test to be performed by less trained persons. In the first step, the sample will have to be taken. In some cases, this may involve the whole product, but in most cases this will involve a part of the product. In the case of a portion of the product, this portion needs to be representative of the whole product. Thus, for instance a part of the flesh or a part of the leaf or the flower may be opted for. Thus, in case of fruit, a piece of skin or a cube of flesh may be taken to perform the test on. If a test is to relate to the quality of a whole batch of the respective product, a representative random sample needs to be taken from the batch. The size of the random sample in relation to the size of the batch then determines reliability. For determining the random sample size that is needed to realize a particular reliability, statistic calculation methods can be taken from specialist literature. Then, based on the random sample, a mixed sample can be made or various tests may be performed on each product sample. Individual determination of each sample then also enables determination of the spread in the batch. After this, the material will have to be fixed and extracted. This can be done by grinding, pressing or disruption of the cell wall in combination with chemicals (e.g. buffers), which ensure that the markers in the sample are not broken down. This may for instance involve FTA paper (Whatman International Ltd., England) but may also involve buffers with proteinase or RNAse inhibitors. The choice for this will depend on the type of sample and can be made by the skilled person. For protein markers, generally other materials will be needed than for RNA markers. In some cases, first a purification of the markers will have to be done, in other cases direct detection of the markers will be possible. Highly suitable for rapid detection of proteins are lateral flow tests, which are directed against the proteins to be detected using antibodies (GenScript Corp. Piscataway, N.J., US; BioGenes GmbH Berlin, Germany). These tests can be easily made (Whatman International Ltd., England) and this technology is already in wide commercial use, for instance in the pregnancy tests obtainable by the consumer.

The invention, in another embodiment, also comprises kits for detecting and predicting the expected quality features in fruit, for instance the hardness of fruit, or predicting the expected harvest window or determining the suitable time of picking the fruit. Such a kit will be specific for a particular variety of fruit and include means for the quantitative detection of the genes, pre-determined for that variety of fruit, that are predictive of the expected value of the quality feature, together with calibration lines of the expression pattern of those corresponding genes for that particular fruit variety, so that the measured expression pattern can be compared with the calibration lines and on the basis thereof a prediction can be made of the expected remaining ripening time and hence also a prediction can be made for the expected time of picking. These calibration lines may also be included in an automated system, so that automatically the values that are generated by the measurement of the expression profile are plotted on these calibration lines and, as outcome, the prediction of the expected value of the quality feature is given. This whole process, including the measurement of the expression profile itself, can take place in an automated system. This automated system then comprises the following elements:

a) means for the measurement of the expression of a number of genes important for the determination of e.g. the hardness of fruit, or corresponding genes, in one or more fruit varieties, such as β-xylosidase (βxyl), polygalacturonidase I and II (PGI and PGII), peroxidase 424/87 (87), Xyloglucan endotransglycosylase (XET), expansin and glucanases such as endo-β-1,4-glucanase, NADP-dependent D-sorbitol-6-phosphate dehydrogenase, alpha amylase;

b) means for the measurement of the expression of control genes, such as for instance house-keeping enzymes, such as phosphoglycerate kinase (PGK) or elongation factor 1alpha (eF1α) or other genes suitable therefor, such as described for instance in Nicot et al., J. Exp. Botany, 56:2907-2914, 2005. All these genes must (can) be taken into account in determining the expression pattern. If one of these genes has the same expression level in all tested samples, that gene is suitable as constitutive gene.

c) means for determining the (relative) expression profile of the genes mentioned under (a);

d) one or more calibration lines that represent the correlation of the expression profiles of one or more of the genes mentioned under a) and the hardness/ripening of the one or more fruit varieties; and e) means for interpreting the measured expression profiles of the one or more fruit varieties in relation to the associated calibration line(s) and on the basis thereof giving an indication about the ripeness of the one or more fruit varieties, which indication also involves an indication of the time that is needed until complete ripening and/or until the optimal time of harvest.

In such an automated system, therefore, several calibration lines may be available, so that the system can be used for several fruit varieties without requiring that each time the proper calibration line be 'loaded'. An additional possibility is for the user to provide the system with data that are specific for the circumstances after harvest of the fruit in question, such as, for instance, the time that the fruit is locally stored, the duration of transport, etc., so that the system can also be flexible as regards those data.

On the basis of the method described, also a test kit may be developed for predicting or determining the value of a specific quality feature for a specific agricultural or horticultural product. For this purpose, the following markers must be available: minimally two markers, with preferably one of the two being a constitutive marker (with which the absolute expression can be derived). The relation between the marker(s) and the feature is laid down in a model (calibration line). This model describes the different expression levels of markers in time. The model can be used inter alma in a computer program to correlate the determined expression levels to the quality/feature of the sample. The quantification of the mRNA (gene expression) levels can take place with for instance quantitative PCR (Applied Biosystems, US). The quantification of proteins can take place using antibodies in for instance a lateral flow immunoassay. The measured data can then be entered (automatically or otherwise) in the computer model, whereupon the result of the test is generated. This result may then be displayed electronically or otherwise.

The invention also comprises a number of markers such as they have been found in the experiments described hereinbelow. This involves especially the marker M8, which is of importance in determining the hardness of fruit; the marker GAST (gibberellic acid stimulated transcript), which is of importance in determining the optimal time of lifting bulbs; and the marker GDSL-motif lipase, which is of importance in determining the vase life of cut flowers. As shown in the Examples, it is possible to use only a part of the genetic information of these markers for demonstrating the presence. The fact is that it is sufficient if primers against these marker target sequences can be composed, so that the marker can be amplified and demonstrated. The invention accordingly comprises the marker sequences M8, GAST and GDSL motif lipase with a nucleotide sequence as indicated in the Examples and in the sequence listing (M8: SEQ ID NO: 13 and 14; GAST: SEQ ID NO: 21 and 22; GDSL-motif lipase: SEQ ID NO: 27 and 28, in which in each case the first represents the nucleotide sequence and the second the amino acid sequence). Both the nucleotide sequence and the protein sequence can, as described above, serve as marker. Because of the fact that minor differences may occur in the sequences in different species or varieties, the invention also relates to sequences being identical to the sequences of SEQ ID NO: 14, 22 and 28, respectively, for more than 70%, preferably more than 80%, more preferably more than 90%, more preferably more than 95% and more preferably more than 98%. The term "identical sequence", as used herein, is usually expressed as a percentage and relates to the percentage of amino acid residues or nucleotides that are identical between two sequences if they are arranged optimally next to each other. For the purpose of this invention, it holds that identity of the sequences as percentage of identical residues or nucleotides has been determined with the well-known BLAST method (Basic Local Alignment Search Tool), which is available to the public via the National Cancer Institute/National Institutes of Health (Bethesda, Md.) and described in numerous publications (see, e.g. Altschul et al., J. Mol. Biol, 215(3), 403-10 (1990)). Preferred parameters for a BLAST comparison of amino acid sequences with BLASTP are gap open 11.0, gap extend 1, Blosum 62 matrix.

Also part of the invention is the use of the markers M8, GAST and GDSL-motif lipase for the determination of quality parameters in plants. More specifically, the use of M8 resides in the determination of the ripeness of fruit, in particular apples and/or pears, the use of GAST in the determination of the optimal time of lifting bulbs, in particular tulip, and the use of MDSL-motif lipase in the determination of the vase life of cut flowers, in particular rose. In these uses, the fragments as shown in the sequence listing can be used, or even, in turn, fragments thereof, but also the whole genes and/or proteins such as they occur by nature in the respective species can be used. On the basis of the sequence information provided herein, a skilled person can easily find them in a genetic databank, or easily isolate them from an organism. The term "antibody" further relates to antigen-binding forms of antibodies (e.g. Fab, F(ab)2). The term "antibody" generally relates to a polypeptide that is substantially encoded by an immunoglobulin gene or immunoglobulin genes, or fragments thereof that specifically recognize an antigen and bind to it. Although the different antibody fragments can be defined in terms of the parts of an intact antibody, the skilled person will realize that such fragments can also be synthesized de novo, either chemically or via recombinant DNA methodology. Thus, the term antibody, as used herein, also comprises antibody fragments such as single chain Fv, also chimeric antibodies (i.e. antibodies that comprise constant and variable regions of different species), humanized antibodies (i.e. those antibodies comprising a CDR (complementarity determining region) not of human origin) and heteroconjugated antibodies (e.g. bispecific antibodies).

EXAMPLES

Housekeeping genes which can be used as constitutive genes/internal control are described inter alia in Nicot et al., Journal of Experimental Botany, Vol 56:2907-2914, 2005.

Example 1

Determination of Correlation of Gene Expression and Fruit Ripening in a Number of Varieties of Apple and Pear Data were collected at various orchards for two pear cultivars, Bon Chretien and Forelle and two apple cultivars, Golden Delicious and Granny Smith. These 4 cultivars were harvested in South Africa for the South African situation (harvest, short storage, conditioned transport to markets such as Europe). Right after harvest (within 48 hours) the value of the various markers was determined in the flesh. For this purpose, mRNA was isolated from a mixed sample of fruits using a CTAB protocol (Plant Molecular Biology Reporter Vol. 11(2), 1993, pp. 113-116). The various markers were identified via the earlier-mentioned techniques of expression profiling and validated via RT-PCR. Use was made of the following primer sets to test all samples:

|  | Forward Primer | Reverse Primer |
|---|---|---|
| PG | GCCCTAATACGGACGGAATTC | AATACAGTCATCACCTGTTCCTATAACC |
| βXYL | AACTAATTGGTGCTGCTGAGGTT | GTCCGGTCTCTGAACTCTGCTT |
| 424/87 | TGGCTCAGGAACATCTTTCATG | CTTGTTGAGTCCAGCAGCAGAG |
| M8 | GGTGGCGGCATGGAGTT | CCCTTTCCCGTAGGCTTCC |
| EF1a | TGGGTTTGAGGGTGACAACA | TGATCAGGTCAAGAGCCTCAAG |
| PGK | CCTGAATTCGCCAAGAAGCT | TGCATGAGCCCTATGAGCAGTA |

Of the same samples, using a standard method and an automatic penetrometer, the firmness of the fruit was determined. In addition, also other physiological parameters were determined, such as: color, starch content, sugar content and malic acid concentration.

This material was followed during the storage in South Africa (for apple a few weeks and for pear approximately 10 days). After this storage, the value of the markers was again determined and a transport simulation was carried out (container transport to e.g. Europe). Then, again, physiological assays were carried out.

Granny Smith (apple) is harvested early during ripening and does not ripen strongly (remains reasonably hard). Forelle is also harvested early but ripens strongly. If the pears are not harvested early, they fall off the tree because they are too heavy. Golden Delicious and Bon Chretien are harvested later in the ripening path and so ripen further on the tree.

For pear, especially the texture markers betaxylosidase (βxyl), polygalacturonase I (PG1), and putative Cell Wall peroxidase 424/87 (87) are relevant. The onset of ripening and the course of ripening can be established by determining when the gene activity of these markers starts to run up (see FIG. 1).

FIG. 1 shows that ripening in the different orchards starts at different moments. Especially the orchards Bo Radyn are ahead of the others. Later ripening may also be caused by the use of particular inhibitors such as e.g. Retain (an ethylene inhibitor). For the graph in FIG. 1, the activities of all three markers have been combined, but this is not strictly necessary. In principle, each of the above-mentioned markers is a good measure. The values of the markers have each time been corrected by comparing them with the activity of a constitutive marker (phosphoglucerate kinase (PGK) or elongation factor 1 alpha (eF1α).

The expected hardness upon arrival in the marketing area (e.g. Europe) can be predicted at the moment of harvest, but also after the first storage, depending on the postharvest treatment, by determining the values of the texture markers during harvest or after the storage and comparing them with a calibration line. The calibration line naturally differs depending on the treatment (e.g. refrigeration temperature, treatment with ethylene inhibitor and the like). It appears that there is an order in the effectiveness of the texture marker, depending on the moment in the ripening path. Early in the ripening path, βxyl is important, then PG1 and then 424/87.

Figure 2A:
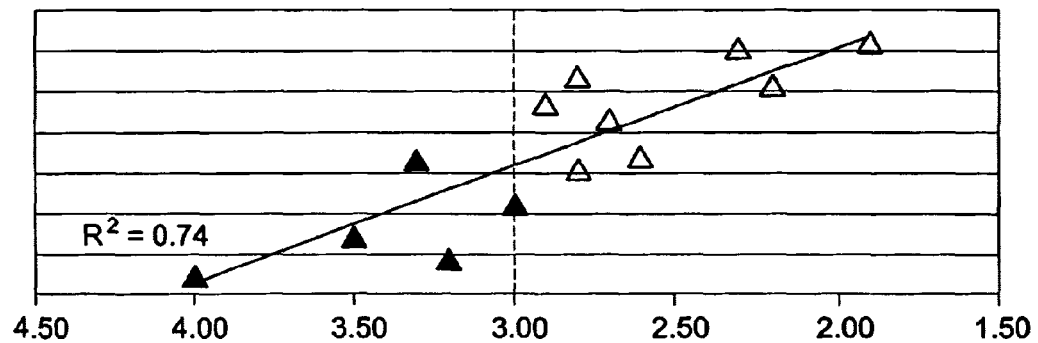
FIG. 2a. Correlation of gene expression of marker 1 (PG1) during harvest and the hardness on the market for pear cv. Bon Chretien.
b. Correlation of gene expression marker 6 (424/87) after short storage and hardness on the market. On the x-axis is indicated the hardness at the end of the storage (the pressure in $N/m^2$ required for pressing-in the fruit) and on the y-axis, logarithmically, the level of expression of the marker. The vertical line indicates the marginal value of the hardness still acceptable for the intended market.
Figure 2B:
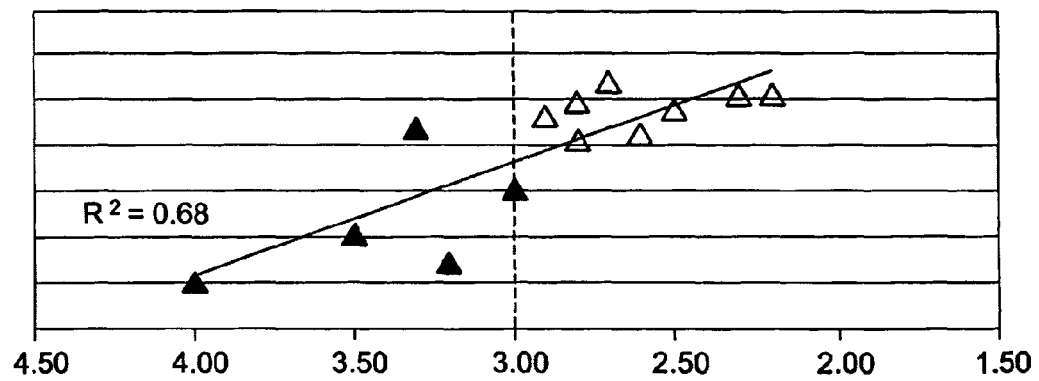
Figure 3A:
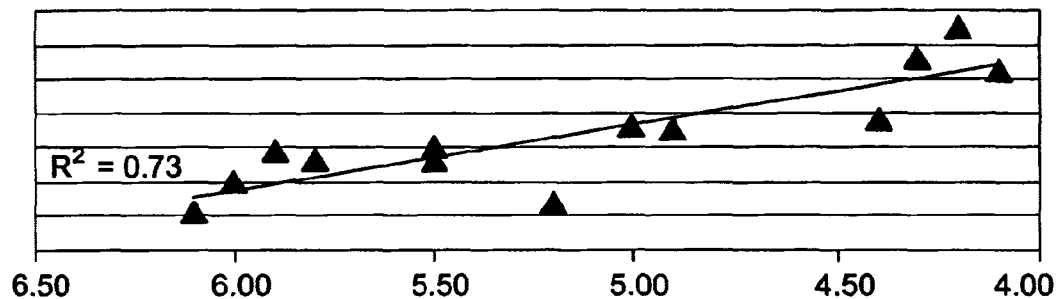
FIG. 3. a. Correlation of gene expression marker 6 (βxyl) during harvest and hardness on the market for pear cv. Forelle.
b. Correlation of gene expression marker 1 (PG1) after short storage and hardness on the market. On the x-axis is indicated the hardness at the end of the storage and on the y-axis, logarithmically, the level of expression of the marker.
Figure 3B:
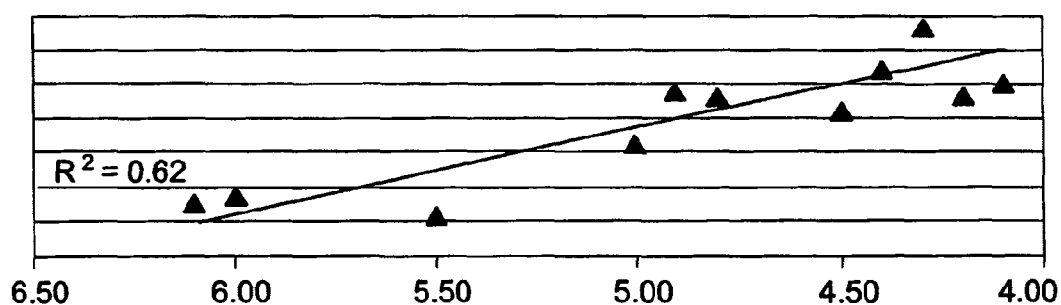

FIG. 2 clearly shows that the hardness in the marketing area has a clear relation with the value of these texture markers at the moment of the measurement. Early on during ripening (harvest) M1 (PG1) gives the best values and later on 424/87 (following brief storage). For Forelle, which is harvested earlier, first βxyl gives the best correlation and then PG1.

Figure 4:
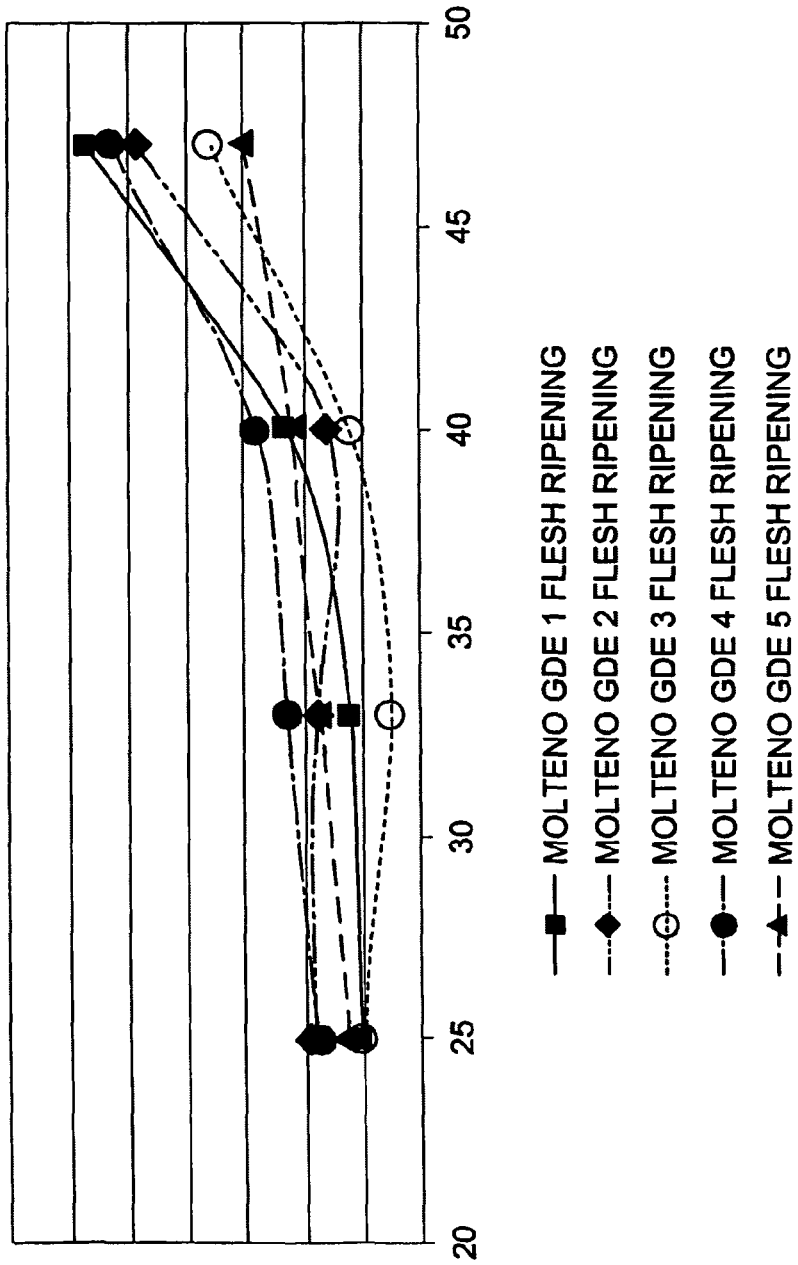
FIG. 4. Course of ripening over time with apple cv. Granny Smith in five orchards. In the diagram, an average value for the totality of the used markers (βxyl and PG) is plotted against time in days.
Figure 5A:
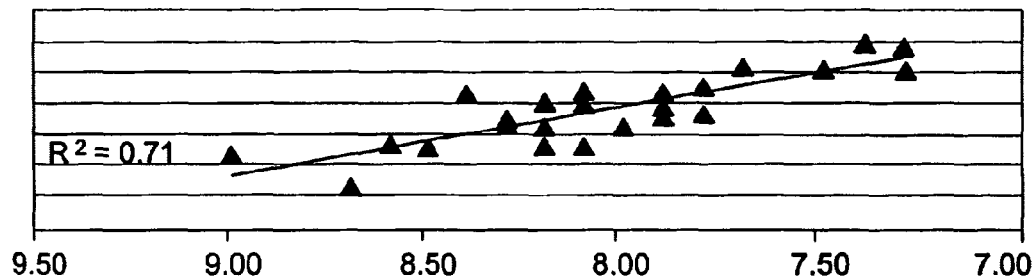
FIG. 5a. Correlation of gene expression βxyl during harvest and hardness on the market for apple cv. Granny Smith.
b. Correlation of gene expression βxyl after short storage and hardness on the market. On the x-axis is indicated the hardness at the end of storage and on the y-axis, logarithmically, the level of expression of the marker.
Figure 5B:
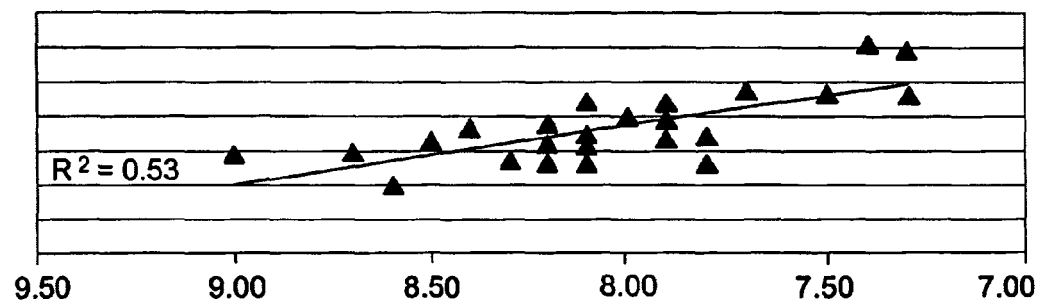
Figure 6:
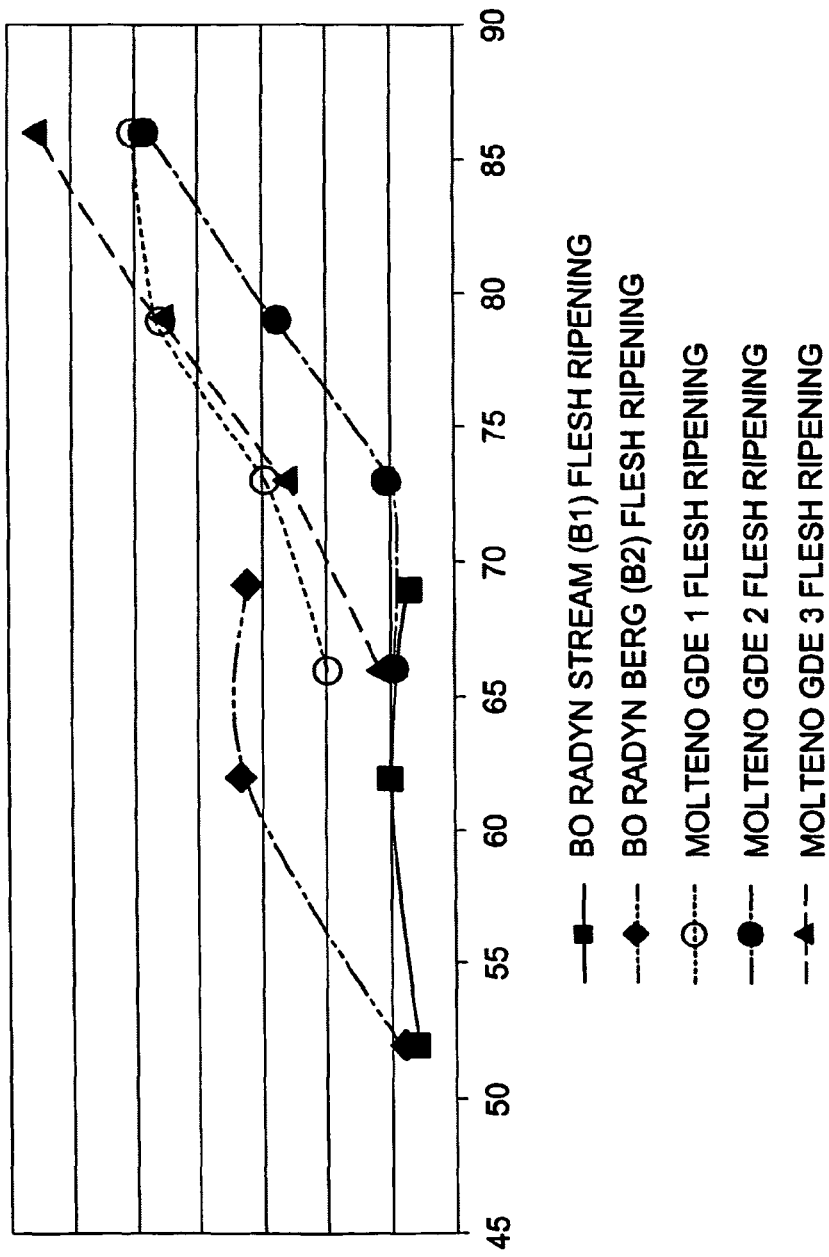
FIG. 6. Course of ripening over time with apple cv. Golden Delicious in five orchards. In the diagram, an average value for the totality of the used markers (βxyl and PG) is plotted against time in days.
Figure 7:
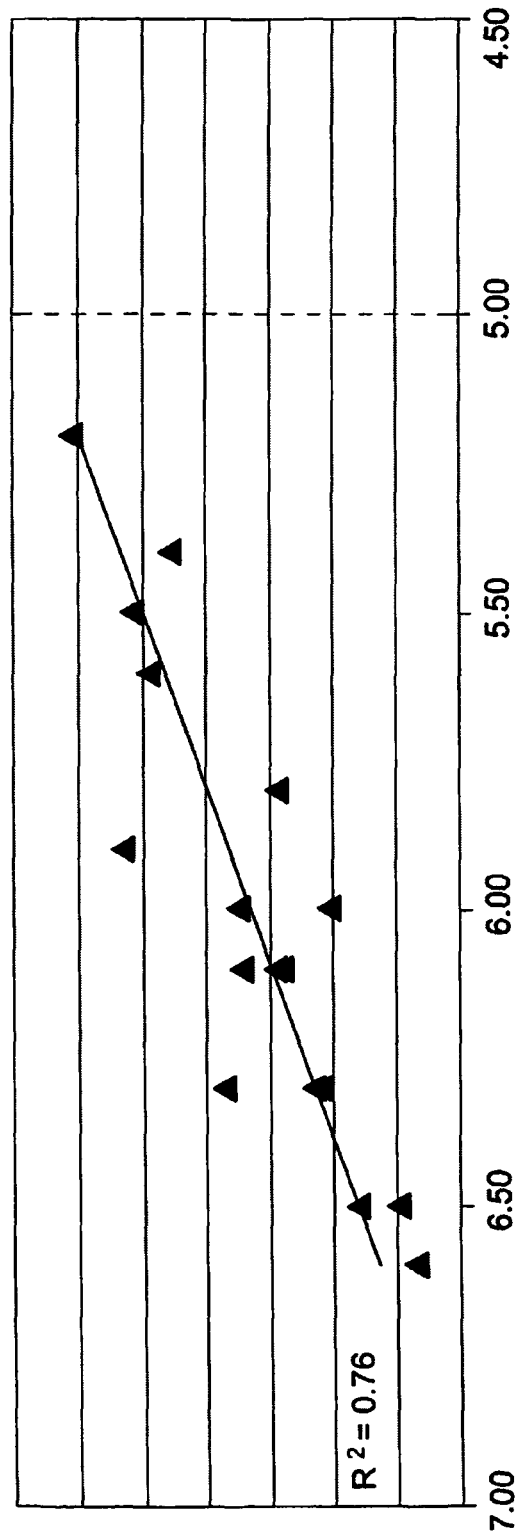
FIG. 7. Correlation of gene expression marker M8 (actin) after short storage and hardness on the market. On the x-axis is indicated the hardness at the end of storage and on the y-axis, logarithmically, the level of expression of the marker. The vertical line indicates the marginal value of the hardness still acceptable for the intended market.

For apple, in principle the same applies. Here too, the ripening stage can be determined via a combination of texture markers. In this case, what is involved is the combination of βxyl and PG1 since in Granny Smith ripening proceeds slowly (see FIG. 4). The expected hardness in the marketing area can especially be predicted via the value of the gene activity of the marker βxyl both during harvest and following brief storage. This is because ripening (and especially softening) in Granny Smith proceeds only very slowly (see FIG. 5). In apple cv. Golden Delicious, the situation is similar again (see FIG. 6). The markers PG1 and βxyl are again jointly of importance, as ripening proceeds very fast and harvesting takes place also later in the ripening process, in this cv another marker is added. This marker M8 has the following sequence (SEQ ID NO:13): gtacatgttcaccactactgctgaacgg-gaaattgtccgtgatatgaaggagaagcttgcatatgttgctctg-gactatgagcaa gaacttgagactgccaagagcagctct-tcagttgagaagaactatgagcttcccgatggccaagtcatcacaa-ttggagct-gag agattccggtgcccagaagtcctat-tcaaccatctcttattggaatggaagctgaggcattcatgagactact-tacaactctatc atgaagtgtgatgtggatatcagaaaa-gacctatatggaaacatcgtgctcagtggtgggtcaactatgttcc-ctggtattg-cag accgtatgagccgggagatcactgctct-tgaccaagcagcatgaagatcaaggttgtagctccaccagagaga-aagtacgcg gggacgatagccaatcagaaaaa-gaaaaaggcacaagtccggcaaaaatgtagcctcagttatg-gcttgttccgt-gagccta aaaccatacccttcactgttcagaagt-cagcagtgagaggccttccactctttccaggtcttctgcttcattc-aaggtgeaagcc agtggcgtcaagaaaatcaagactgc-caccccatatggaactggtggcggcatggagttgaggaacggtgttg-atgc-ctctggg aggaagcctacgggaaagggtgtctaccagtttgtagacaagtac. The marker M8 has the highest homology score with an actin from pear. FIG. 7 gives a correlation of the activity of this gene in relation to hardness after the first storage.

Example 2

Determination of the Optimal Time of Lifting Tulips by Correlation with Flowering Quality after Harvest with Gene Expression Around the Time of Harvest During a period of four years, three tulip cultivars, cv 'Apeldoorn', cv 'Leen van de Mark' and cv 'Prominence', were each time sampled on the same growing lots. Sampling was carried out at different times in the season, from 6 to 7 weeks before the expected date of lifting with an interval of 2 weeks, at least 1 week before the established lifting date, at the moment of lifting, and a week after. The growing lots were each time sampled in the morning, after which during the rest of the day sample processing took place. From the outermost bulb scale, a piece of tissue of a size of 1 cm$^2$ was taken, which was fixed in liquid nitrogen immediately. Next, in this tissue, the gene expression was determined of a sizeable number of genes on the basis of which 3 markers were identified that have a relation with the time of harvest during all measured seasons and in each cultivar.

To be able to establish the optimal time of lifting in relation to the product quality in the postharvest path, a portion of the bulbs from the field sample was reserved for storage. After storage, these bulbs were subsequently forced and planted with a view to assessing the quality of the resulting flower and stem and correlating the value of the markers with the obtained values of the flowering quality parameters. Objective quality parameters in the assessment were the weight of the flower and the length of the stem.

Validation of these markers was subsequently carried out during two extra seasons, when also other growing locations were sampled. For that purpose, each time a mixed sample of 10 bulbs was taken for the isolation of RNA in which the concentration of the markers was established using quantitative PCR.

In the PCR procedure, the following primer combinations were used, corresponding to the nucleotide sequences of the three markers isolated from cv 'Prominence':

| Marker | forward primer | reverse primer |
|---|---|---|
| GAST | 5'-GGCACCTACGGCAACTATGATAG-3' | 5'-CACTTGCGAGCACCATGATG-3' |
| EIF4a | 5'-CGTCCCGTGTCACAAAGTTG-3' | 5'-CCATCGTATCGGTCGTAGTGG-3' |
| EFIA | 5'-TTGATATTGCTCTCTGGAAGTTTGAG-3' | 5'-AGTTCCAGTAATCATGTTCTTAATGAAGTC-3' |

Figure 11:
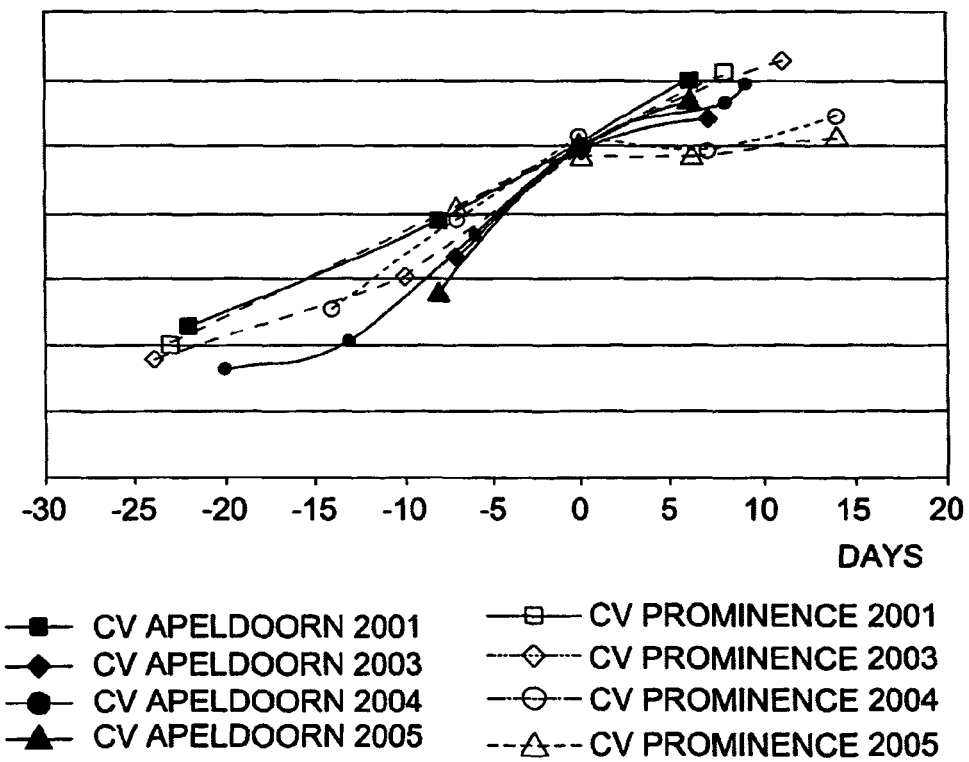
FIG. 11. Expression (on the y-axis) of GAST in tulip in relation to the time of lifting. On the x-axis are indicated the number of days from the optimal time of lifting. The pattern of expression of GAST in 4 years cv Apeldoorn and cv Prominence is plotted.

The course of the combined measuring values of the markers for the cultivars 'Prominence' and 'Apeldoorn' is represented in FIG. 11. From three weeks before the optimal time of harvest up to the optimal time of harvest that was determined in flowering tests, the course of the markers, plotted logarithmically against time, exhibits a virtually linear and reproducible pattern. The value of the marker was correlated with the value for the parameter of the flowering quality to determine at which value of the marker the optimal time of lifting was reached. For a particular cultivar, the linear course of the markers is identical; among the cultivars there is a difference in linear course. By combining measuring values from different years, per cultivar a reliable calibration line can be determined. On the basis of this calibration line, it is possible to predict the optimal time of lifting in a new season on the basis of only 1 or 2 measurements of samples that were taken in the field between 2 weeks and the expected time of lifting.

The marker GAST has the following nucleotide sequence (SEQ ID NO:21):

```
gatcatccagttactaagctaagcaagccctccttcctcaacttatcaat
gacttcatccacctccatcctgacatcccttgtgcttctcttcctccttg
tcggtctcgtcgagcccgcctggagattgaacccggaaacgggatagaa
aggtctcttctaggtgggctaagtaagcaactcttccgaactatcactaa
tcagtatgttggtattcttagagagaagttaaccatagattgttatgatg
atcaggctgcggtgcggcgtgcttggtgaggtgcagcgagtcatcaaggc
cgaatctgtscaagagggcgtgcgggacatgctgtgcaaggtgcagctgc
gtcccaccgggcacctacggcaactatgatagctgcccttgttacgcttc
actcaccacccatcatggtgctcgcaagtgcccttaaacatgaagaataa
attggtgtgtcataggtgatgaaagtgggttcgcttgttcgatatatata
tatgtaataaaacgttcaaacaaactcagttattcgaataaagagg
```

The expression of the GAST marker becomes properly measurable from 3 weeks before the time of harvest. Prior to this point in time no reliable value for this marker can be obtained. From three weeks before harvest, expression increases exponentially and at the optimal time of harvest reaches a value that is the same in the three measured cultivars. After the optimal moment of harvest, this marker obtains a constant value.

The other markers, EIF4a and EFIA, are constitutive genes whose expression does not vary at any of the measured times before, during and after harvest of tulip bulbs. The average values of these markers are used for normalization to allow comparison of measured series.

Example 3

Determination of Correlation of Gene Expression and Quality of Rose Cut Flowers

Gene expression data were used to predict the vase life of rose. In practice, it appears that some roses keep well on the vase at the consumer for only 5 days whereas other roses (of the same cultivar) sometimes keep well for as many as 10 days. This is often due to their being harvested while too unripe, which compromises quality.

Figure 12:
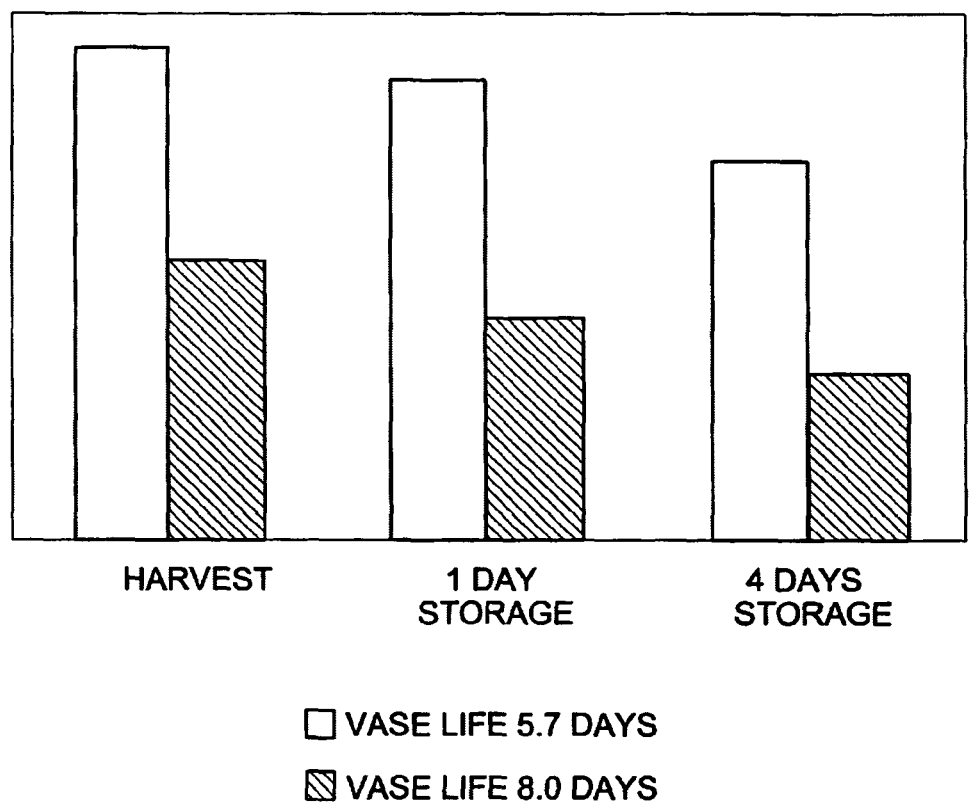
FIG. 12. Quality marker for vase life in rose. Expression (on the y-axis) of the GDSL-motif lipase in rose with a vase life of 5.7 days and a vase life of 8.0 days. The expression of the marker is lower in the roses of good keeping quality than in the roses of poor keeping quality. Harvest is the moment directly after cutting, storage is at 4° C. on water, for 1 day and for 4 days.

It was investigated of which gene or which genes the expression exhibits a good correlation with the time of harvest and quality. With the gene expression data, using the earlier-mentioned techniques, a correlation was carried out with the vase life of the rose. Determining the relative expression in flower petals during and after harvest enabled making a prediction about the expected vase life of the rose. The gene found to be useful for this purpose is a GDSL-motif lipase in combination with a constitutive marker, in this case elongation factor 1α, see FIG. 12. Also when the roses are stored at 4° C., the difference in vase life remains measurable. The values found are consistent between different cultivars and between different years of harvest. This marker was validated with RT-PCR. Use was made of the following primer sets to test all samples:

The GDSL-motif lipase has the following sequence (the encoding reverse complementary strand is represented in SEQ ID NO:27):

```
gtactacaatactactaaataccgtattatcatattgccactccatggt
ggaagtagaaacatccactgtagaaagcaaaatgaagacttacctccag
aatgcaattctaaacaacctaataagtaataactatacttagttgggca
caaacaaatatagtagctggggataaagccatatatcaacctatctaaa
gtgataggaacctagatttataataattttatgccctagctttcatata
ttaattgaaggaaaattaaggaaactgggtcaggacacgtttgactatg
taatcagagatgatctggtttgctttctctgtgggatggaaggagtccc
agaagatgtatttgcttgcatcagtgcatgtgaacatgttgtttcggtt
gcatgcatatcccatctcaaacattcctgtggcacaacaagccactgat
gtcacctcaaaaccgtaaaaagaaggccttcttatcatatacaggaaaa
caaaataaggatttgagaacaccaatttgcttccaggaagctctttatt
gaggctgacggtcaacttattcagcttgtcattgaactccaaagccaca
tcgttgtaattcgaaatgcagtcatttccatccatgatattactggttc
tctctaatggcaagcatcccattggaggcagtcctcccacggaaatttt
ccgagctccgagcttgtagagttccttcacgaaattcgctgcgattccg
atgagaaagtcttggtattgggaggtagtgtattggggatgatcggcct
gatggtggaaatgtgg
```

The marker has the highest homology score with a possible GDSL-motif lipase/hydrolase from Arabidopsis (At2g04570). In Arabidopsis this gene is specifically expressed in buds and stomata.

Example 4

Determination of Correlation of Gene Expression and Fruit Ripening in a Number of Varieties of Apple and Pear Data were collected at various orchards for pear cultivar Conference and apple cultivar Kanzi. These 2 cultivars were harvested in the Netherlands for the Dutch situation (harvest, conditioned storage (4-10 months)). Right after harvest (within 48 hours) the value of the various markers was determined in the flesh. For this purpose, mRNA was isolated from a mixed sample of fruits using a CTAB protocol (Plant Molecular Biology Reporter Vol. 11(2), 1993, pp. 113-116). The various markers were identified via the earlier-mentioned techniques of expression profiling and validated via RT-PCR. Use was made of the following primer sets to test all samples:

|  | Forward Primer | Reverse Primer |
|---|---|---|
| GDSL-motif lipase | AGGATTTGAGAACACCAATTTGC | GAGTTCAATGACAAGCTGAATAAGTTG |
| EF1 | TGGTGTCAAGCAGATGATTTGC | TTCATCGTACCTTGCCTTTGAG |

|     | Forward Primer | Reverse Primer |
| --- | --- | --- |
| PG | GCCCTAATACGGACGGAATTC | AATACAGTCATCACCTGTTCCTATAACC |
| βXYL | AACTAATTGGTGCTGCTGAGGTT | GTCCGGTCTCTGAACTCTGCTT |
| EF1a | TGGGTTTGAGGGTGACAACA | TGATCAGGTCAAGAGCCTCAAG |
| PGK | CCTGAATTCGCCAAGAAGCT | TGCATGAGCCCTATGAGCAGTA |

Of the same samples, using a standard method and an automatic penetrometer, the firmness of the fruit was determined. In addition, also other physiological parameters were determined, such as: color, starch content, sugar content and malic acid concentration.

This material was followed during storage in the Netherlands in cold stores of low oxygen concentration, samples were taken after approximately 5 months' storage. Of these samples, again physiological determinations were carried out.

Figure 8:
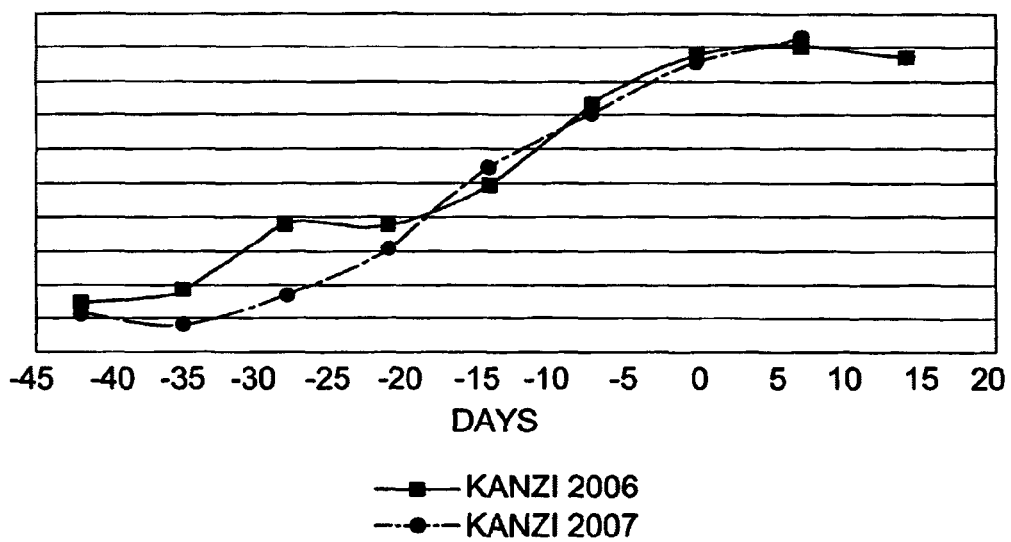
FIG. 8. Apple cultivar Kanzi was sampled each week during season 2006 and 2007. On the x-axis are the number of days relative to the optimal harvesting moment (determined with physiological parameters). On the y-axis is indicated the level of expression of beta-Xylosidase.

For pear and apple, especially the texture markers beta-xylosidase (βxyl) and polygalacturonase I (PG1) proved relevant to the Dutch situation. The onset of ripening and the course of ripening can be established by determining when the gene activity of these markers starts to run up (see FIG. 8). In FIG. 8 the expression of βxyl is plotted against time in days. Taken as origin was the optimal time of harvest (established with physiological parameters) because this enables comparisons between different years. In FIG. 8 it can be clearly seen that the course of this marker is almost identical between different years and can be used well to establish the optimal time of harvest. In FIG. 8 a marker was used, but the expression pattern of PG proceeds in the same manner and can optionally be used together with βxyl to obtain a still better resolution. The values of the markers were each time corrected by comparing them with the activity of a constitutive marker (phosphoglucerate kinase (PGK) or elongation factor 1 alpha (eF1α).

The expected hardness upon leaving the cold store after months of storage can be predicted at the moment of harvest, depending on the postharvest treatment, by determining the values of the texture markers after storage and comparing them with a calibration line. The calibration line naturally differs depending on the treatment (e.g. refrigeration temperature, treatment with ethylene inhibitor and the like).

Figure 9A:
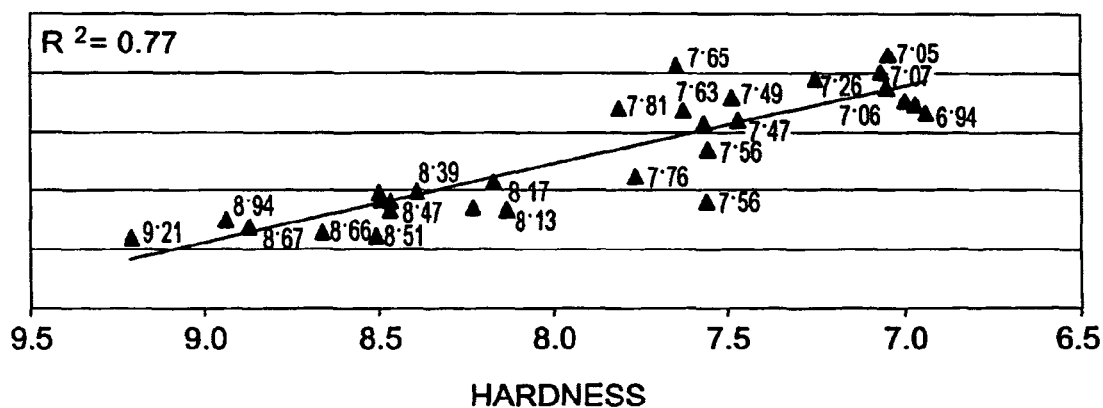
FIG. 9. Apple cv. Kanzi flesh markers during harvest versus firmness at the end of storage (EOS). The expression of the marker is plotted against the firmness of the apple in kilograms. In panel A for marker PG, in panel B for marker beta-xylosidase.
Figure 9B:
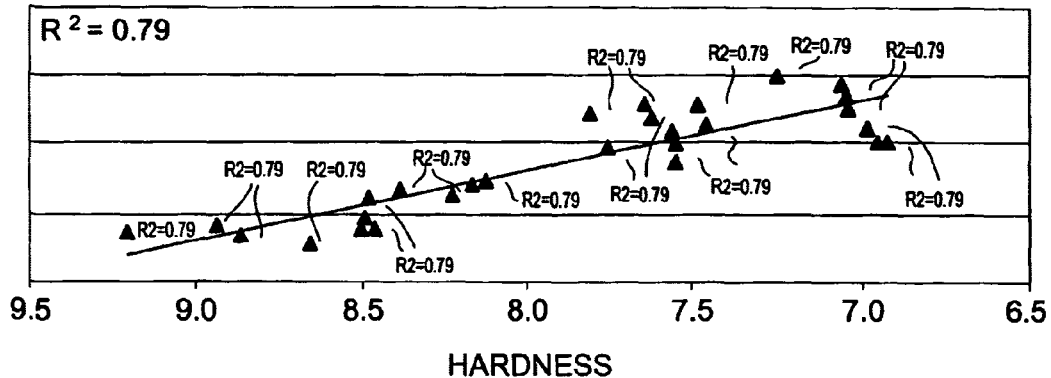
Figure 10A:
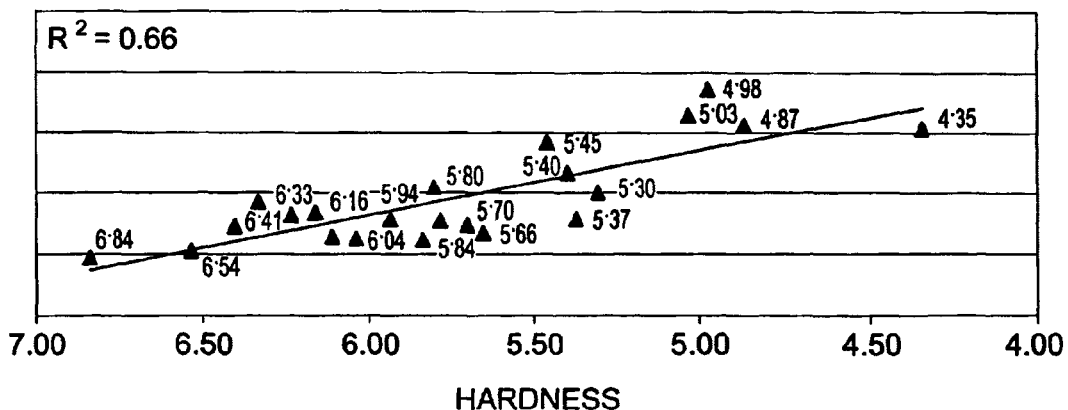
FIG. 10. Pear cv Conference flesh markers during harvest versus firmness at the end of storage (EOS). The expression of the marker is plotted against the hardness of the pear in kilograms. In panel A for marker PG, in panel B for marker beta-xylosidase.
Figure 10B:
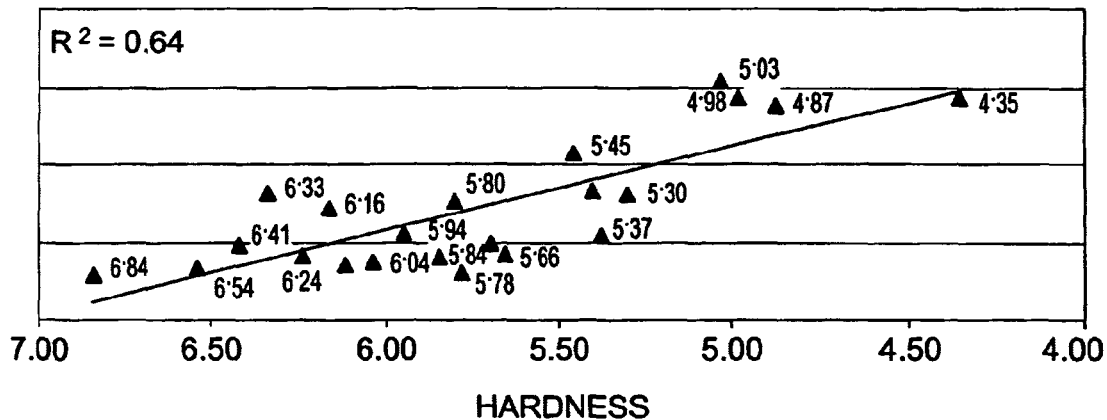

FIGS. 9 and 10 clearly show that the hardness after storage of apple and pear has a clear relation with the value of these texture markers at the time of harvest. This holds again for both PG and βxyl.

The invention claimed is:

1. A method for determining genetic or protein/enzymatic markers for, at the time of harvest, predicting the expected value of a relevant quality feature for an agricultural and/or horticultural product at a given time during or after harvest, comprising the steps of:
 a. defining a quantitative or relative measuring value for the relevant quality feature for the specific agricultural or horticultural product;
 b. determining the expression levels of a set of genes, preferably related to the specific quality feature, or the protein concentration of a set of proteins/enzymes, preferably related to the specific quality feature, at several points in time before, during and after harvest;
 c determining the correlation of the expression levels determined in b) or the protein concentrations determined in b) with the value (according to the definition determined in a)) of the quality feature specific for that agricultural or horticultural product at a given time during or after harvest; and
 d. identification of those genes from b) that show a rising or falling expression level profile or those proteins/enzymes from b) that show a rising or falling concentration course and have a correlation coefficient with the value of the quality factor at a given time during or after harvest, in the range of 0.3-1, preferably in the range of 0.4-1, more preferably in the range of 0.5-1, more preferably in the range of 0.6-1, more preferably in the range of 0.7-1, more preferably in the range of 0.8-1, most preferably in the range of 0.9-1;
 e. determining a calibration line which, for a specific postharvest path, fixes the relation between gene activity of the genes or the value of the concentration of the protein/enzyme at the time of harvest with the highest correlation coefficient determined in 1d and the value of the specific quality feature at a given time during or after harvest for the specific agricultural or horticultural product;
 f. and optionally determining specific calibration lines based on the above procedure for different types of postharvest paths.

2. A method for predicting the expected value of a specific quality feature for a specific agricultural or horticultural product at the end of the postharvest path, comprising the steps of:
 a. determining the expression level of one or more genetic markers or the concentration of one or more protein/enzymatic markers in the fruit to be tested before the postharvest path or during the postharvest path;
 b. predicting the expected value of the specific quality feature for the specific agricultural or horticultural product after the postharvest path based on the course of the calibration line determined according to claim 1, which is intended for that specific measuring moment and that specific postharvest situation, with the gene expression or protein concentration measured in a), whereby the value of the specific quality feature predicted on the basis of the specific expression or protein concentration can be read from the graph of the specific calibration line.

3. A method for predicting the expected value of the quality in respect of a specific quality feature for a specific agricultural or horticultural product at the end of the postharvest path, comprising the steps of:
   a. defining the range of values considered acceptable for the specific agricultural or horticultural product by the market for the specific quality feature;
   b. based on the value for a specific quality feature determined according to claim 2 and the range defined in a), considering the predicted quality as acceptable or non-acceptable for that quality feature.

4. A method according to claim 2 wherein the specific quality feature is the ripeness of fruit, comprising determining the activity of marker M8.

5. The method according to claim 4, wherein the marker comprises the amino acid sequence of SEQ ID NO: 14, or a sequence which is at least 70% identical thereto.

6. A method according to claim 2 wherein the specific quality feature is the vase life of cut flowers comprising determining the activity of marker GDSL motif lipase.

7. The method according to claim 6, wherein the marker comprises the amino acid sequence of SEQ ID NO: 27, or a sequence which is at least 70% identical thereto.

8. A method for determining the starting point in time and the end point in time of the optimal harvest time of an agricultural or horticultural product, comprising the steps of:
   a. determining the expression level profile of one or more genetic markers or the concentration course of one or more protein/enzymatic markers with the highest correlation coefficient as determined according to step d) of claim 1 in the agricultural or horticultural product to be tested, at several harvest points in time;
   b. determining the value of the specific quality feature that belongs to the value of the gene activity of the gene or of the concentration of the marker protein/enzyme in the time path of the harvest;
   c. determining the first moment in time that a value of the specific quality feature that falls within the acceptable quality range defined by the values considered acceptable for the specific agricultural or horticultural product is reached, and designating this moment in time as the starting point in time of the optimal harvest time;
   d. determining the last moment in time that a value of the specific quality feature that falls within the acceptable quality range defined by the values considered acceptable for the specific agricultural or horticultural product is reached, and designating this moment in time as the end point in time of the optimal harvest time.

9. A method according to claim 8 wherein the specific quality feature is the optimal lifting time for bulbs comprising determining the activity of marker GAST.

10. The method according to claim 9, wherein the marker comprises the amino acid sequence of SEQ ID NO: 22, or a sequence which is at least 70% identical thereto.

11. The method according to claim 1, wherein the said agricultural or horticultural product is selected from the group consisting of fruit, vegetables, potatoes, seeds (such as grain), nuts, cut flowers, bulbs, ornamental pot plants and harvestable herbs.

12. The method according to claim 11, wherein said agricultural or horticultural product is fruit and is selected from the group consisting of apple, pear, citrus fruits such as orange, mandarin, lemon and minneola, melon, tomato, peach, plum, grape, currant, gooseberry, blackberry, raspberry, cherry, pineapple, mango, kiwi, litchi, banana, paprika, and avocado, including all varieties and cultivars thereof.

13. The method according to claim 12, wherein said quality feature is selected from the group consisting of the hardness of the fruit, the sweetness of the fruit, the color of the fruit, the size of the fruit, and a combination of one or more of these.

14. The method according to claim 13, wherein the quality feature is hardness of the fruit, and the fruit is apple or pear and wherein the genetic and/or protein markers are selected from the group consisting of M8, β-xylosidase (βxyl), polygalacturonidase I and II (PGI and PGII), putative cell wall peroxidase 424/87 (87), xyloglucan endotransglycosylase (XET), expansin and glucanases such as endo-β-1,4-glucanase and the genes coding therefor.

15. The method according to claim 11, wherein said agricultural or horticultural product is a vegetable and is selected from lettuce, tomato, potato, tapioca, yam, any type of cabbage, carrots, winter carrot and pulses.

16. The method according to claim 11, wherein the quality feature is the vase life of cut flowers, and the cut flower is rose and wherein the genetic and/or protein markers comprise at least the marker GDSL motif lipase and/or the gene coding therefor.

17. The method according to claim 11, wherein the quality feature is the optimal lifting time of bulbs, and the bulb is tulip and wherein the genetic and/or protein markers comprise at least the marker GAST and/or the gene coding therefor.

18. A method for determining genetic or protein/enzymatic markers for, during a specific postharvest path, predicting the expected value of the relevant quality feature for that agricultural or horticultural product, comprising the steps of:
   a. defining a quantitative or relative measuring value for the relevant quality feature for the specific agricultural or horticultural product;
   b. determining the expression levels of a set of genes, preferably related to the specific quality feature, or the protein concentration of a set of proteins/enzymes, preferably related to the specific quality feature, at several points in time during the postharvest path;
   c. determining the correlation of the expression levels determined in b) or the protein concentrations determined in b) with the value (according to the definition determined in a)) of the quality feature specific for that agricultural or horticultural product at a given time after harvest; and
   d. identification of those genes from b) that show a rising or falling expression level profile or those proteins/enzymes from b) that show a rising or falling concentration course and have a correlation coefficient with the value of the quality factor at a given time after harvest, in the range of 0.3-1, preferably in the range of 0.4-1, more preferably in the range of 0.5-1, more preferably in the range of 0.6-1, more preferably in the range of 0.7-1, more preferably in the range of 0.8-1, most preferably in the range of 0.9-1;
   e. determining a calibration line which, for said specific postharvest path, fixes the relation between gene activity of the genes or the value of the concentration of the protein/enzyme during said postharvest path with the highest correlation coefficient determined in 1d and the value of the specific quality feature at a given time during or after harvest for the specific agricultural or horticultural product;
   f. and optionally determining specific calibration lines based on the above procedure for different types of postharvest paths.

* * * * *

UNITED STATES PATENT AND TRADEMARK OFFICE
CERTIFICATE OF CORRECTION

PATENT NO. : 8,498,819 B2
APPLICATION NO. : 12/527888
DATED : July 30, 2013
INVENTOR(S) : De Boer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 653 days.

Signed and Sealed this
Fifteenth Day of September, 2015

Michelle K. Lee
*Director of the United States Patent and Trademark Office*

SEQUENCE LISTING

```
<160> NUMBER OF SEQ ID NOS: 28

<210> SEQ ID NO 1
<211> LENGTH: 21
<212> TYPE: DNA
<213> ORGANISM: Artificial
<220> FEATURE:
<223> OTHER INFORMATION: ptimer PG forward

<400> SEQUENCE: 1
gccctaatac ggacggaatt c                                              21

<210> SEQ ID NO 2
<211> LENGTH: 28
<212> TYPE: DNA
<213> ORGANISM: Artificial
<220> FEATURE:
<223> OTHER INFORMATION: primer PG reverse

<400> SEQUENCE: 2
aatacagtca tcacctgttc ctataacc                                       28

<210> SEQ ID NO 3
<211> LENGTH: 23
<212> TYPE: DNA
<213> ORGANISM: Artificial
<220> FEATURE:
<223> OTHER INFORMATION: primer beta-xyl forward

<400> SEQUENCE: 3
aactaattgg tgctgctgag gtt                                            23
```

```
<210> SEQ ID NO 4
<211> LENGTH: 22
<212> TYPE: DNA
<213> ORGANISM: Artificial
<220> FEATURE:
<223> OTHER INFORMATION: primer beta-xyl reverse

<400> SEQUENCE: 4
gtccggtctc tgaactctgc tt                                              22

<210> SEQ ID NO 5
<211> LENGTH: 22
<212> TYPE: DNA
<213> ORGANISM: Artificial
<220> FEATURE:
<223> OTHER INFORMATION: primer 42/87 forward

<400> SEQUENCE: 5
tggctcagga acatctttca tg                                              22

<210> SEQ ID NO 6
<211> LENGTH: 22
<212> TYPE: DNA
<213> ORGANISM: Artificial
<220> FEATURE:
<223> OTHER INFORMATION: primer 424/87 reverse

<400> SEQUENCE: 6
cttgttgagt ccagcagcag ag                                              22

<210> SEQ ID NO 7
<211> LENGTH: 17
<212> TYPE: DNA
<213> ORGANISM: Artificial
<220> FEATURE:
<223> OTHER INFORMATION: primer M8 forward

<400> SEQUENCE: 7
ggtggcggca tggagtt                                                    17

<210> SEQ ID NO 8
<211> LENGTH: 19
<212> TYPE: DNA
<213> ORGANISM: Artificial
<220> FEATURE:
<223> OTHER INFORMATION: primer M8 reverse

<400> SEQUENCE: 8
ccctttcccg taggcttcc                                                  19

<210> SEQ ID NO 9
<211> LENGTH: 20
<212> TYPE: DNA
<213> ORGANISM: Artificial
<220> FEATURE:
<223> OTHER INFORMATION: primer EF1a forward

<400> SEQUENCE: 9
tgggtttgag ggtgacaaca                                                 20

<210> SEQ ID NO 10
<211> LENGTH: 22
<212> TYPE: DNA
<213> ORGANISM: Artificial
<220> FEATURE:
<223> OTHER INFORMATION: primer EF1a reverse
```

```
<400> SEQUENCE: 10
tgatcaggtc aagagcctca ag                                          22

<210> SEQ ID NO 11
<211> LENGTH: 20
<212> TYPE: DNA
<213> ORGANISM: Artificial
<220> FEATURE:
<223> OTHER INFORMATION: primer PGK fw

<400> SEQUENCE: 11
cctgaattcg ccaagaagct                                             20

<210> SEQ ID NO 12
<211> LENGTH: 22
<212> TYPE: DNA
<213> ORGANISM: Artificial
<220> FEATURE:
<223> OTHER INFORMATION: primer PGK reverse

<400> SEQUENCE: 12
tgcatgagcc ctatgagcag ta                                          22

<210> SEQ ID NO 13
<211> LENGTH: 723
<212> TYPE: DNA
<213> ORGANISM: Malus sp.
<220> FEATURE:
<221> NAME/KEY: CDS
<222> LOCATION: (2)..(502)

<400> SEQUENCE: 13 g tac atg ttc acc act act gct gaa cgg gaa att gtc cgt gat atg aag    49
  Tyr Met Phe Thr Thr Thr Ala Glu Arg Glu Ile Val Arg Asp Met Lys
   1               5                  10                  15 gag aag ctt gca tat gtt gct ctg gac tat gag caa gaa ctt gag act      97
Glu Lys Leu Ala Tyr Val Ala Leu Asp Tyr Glu Gln Glu Leu Glu Thr
             20                  25                  30 gcc aag agc agc tct tca gtt gag aag aac tat gag ctt ccc gat ggc     145
Ala Lys Ser Ser Ser Ser Val Glu Lys Asn Tyr Glu Leu Pro Asp Gly
         35                  40                  45 caa gtc atc aca att gga gct gag aga ttc cgg tgc cca gaa gtc ctc     193
Gln Val Ile Thr Ile Gly Ala Glu Arg Phe Arg Cys Pro Glu Val Leu
     50                  55                  60 ttt caa cca tct ctt att gga atg gaa gct gct ggc att cat gag act     241
Phe Gln Pro Ser Leu Ile Gly Met Glu Ala Ala Gly Ile His Glu Thr
 65                  70                  75                  80 act tac aac tct atc atg aag tgt gat gtg gat atc aga aaa gac cta     289
Thr Tyr Asn Ser Ile Met Lys Cys Asp Val Asp Ile Arg Lys Asp Leu
                 85                  90                  95 tat gga aac atc gtg ctc agt ggt ggg tca act atg ttc cct ggt att     337
Tyr Gly Asn Ile Val Leu Ser Gly Gly Ser Thr Met Phe Pro Gly Ile
            100                 105                 110 gca gac cgt atg agc cgg gag atc act gct ctt gct cca agc agc atg     385
Ala Asp Arg Met Ser Arg Glu Ile Thr Ala Leu Ala Pro Ser Ser Met
        115                 120                 125 aag atc aag gtt gta gct cca cca gag aga aag tac gcg ggg acg ata     433
Lys Ile Lys Val Val Ala Pro Pro Glu Arg Lys Tyr Ala Gly Thr Ile
    130                 135                 140 gcc aat cag aaa aag aaa aag gca caa gtc cgg caa aaa tgt ctg cct     481
Ala Asn Gln Lys Lys Lys Lys Ala Gln Val Arg Gln Lys Cys Leu Pro
145                 150                 155                 160 cag tta tgg ctt gtt ccg tga gcctaaaacc atctcccttc actgttcaga       532
Gln Leu Trp Leu Val Pro
```

-continued

```
Gln Leu Trp Leu Val Pro
            165 agtcagcagt gagaggcctt ccctctcttt ccaggtcttc tgcttcattc aaggtgcaag    592 ccagtggcgt caagaaaatc aagactgcca ccccatatgg aactggtggc ggcatggagt    652 tgaggaacgg tgttgatgcc tctgggagga agcctacggg aaagggtgtc taccagtttg    712 tagacaagta c                                                        723

<210> SEQ ID NO 14
<211> LENGTH: 166
<212> TYPE: PRT
<213> ORGANISM: Malus sp.

<400> SEQUENCE: 14

Tyr Met Phe Thr Thr Thr Ala Glu Arg Glu Ile Val Arg Asp Met Lys
1               5                   10                  15

Glu Lys Leu Ala Tyr Val Ala Leu Asp Tyr Glu Gln Glu Leu Glu Thr
            20                  25                  30

Ala Lys Ser Ser Ser Ser Val Glu Lys Asn Tyr Glu Leu Pro Asp Gly
        35                  40                  45

Gln Val Ile Thr Ile Gly Ala Glu Arg Phe Arg Cys Pro Glu Val Leu
    50                  55                  60

Phe Gln Pro Ser Leu Ile Gly Met Glu Ala Ala Gly Ile His Glu Thr
65                  70                  75                  80

Thr Tyr Asn Ser Ile Met Lys Cys Asp Val Asp Ile Arg Lys Asp Leu
                85                  90                  95

Tyr Gly Asn Ile Val Leu Ser Gly Gly Ser Thr Met Phe Pro Gly Ile
            100                 105                 110

Ala Asp Arg Met Ser Arg Glu Ile Thr Ala Leu Ala Pro Ser Ser Met
        115                 120                 125

Lys Ile Lys Val Val Ala Pro Pro Glu Arg Lys Tyr Ala Gly Thr Ile
    130                 135                 140

Ala Asn Gln Lys Lys Lys Ala Gln Val Arg Gln Lys Cys Leu Pro
145                 150                 155                 160

Gln Leu Trp Leu Val Pro
            165

<210> SEQ ID NO 15
<211> LENGTH: 23
<212> TYPE: DNA
<213> ORGANISM: Artificial
<220> FEATURE:
<223> OTHER INFORMATION: primer GAST forward

<400> SEQUENCE: 15
ggcacctacg gcaactatga tag                                            23

<210> SEQ ID NO 16
<211> LENGTH: 20
<212> TYPE: DNA
<213> ORGANISM: Artificial
<220> FEATURE:
<223> OTHER INFORMATION: primer GAST reverse

<400> SEQUENCE: 16
cacttgcgag caccatgatg                                                20

<210> SEQ ID NO 17
<211> LENGTH: 20
<212> TYPE: DNA
```

<213> ORGANISM: Artificial
<220> FEATURE:
<223> OTHER INFORMATION: primer EIF4a forward

<400> SEQUENCE: 17
cgtcccgtgt cacaaagttg                                          20

<210> SEQ ID NO 18
<211> LENGTH: 21
<212> TYPE: DNA
<213> ORGANISM: Artificial
<220> FEATURE:
<223> OTHER INFORMATION: primer EIF4a reverse

<400> SEQUENCE: 18
ccatcgtatc ggtcgtagtg g                                        21

<210> SEQ ID NO 19
<211> LENGTH: 26
<212> TYPE: DNA
<213> ORGANISM: Artificial
<220> FEATURE:
<223> OTHER INFORMATION: primer EFIA forward

<400> SEQUENCE: 19
ttgatattgc tctctggaag tttgag                                   26

<210> SEQ ID NO 20
<211> LENGTH: 30
<212> TYPE: DNA
<213> ORGANISM: Artificial
<220> FEATURE:
<223> OTHER INFORMATION: primer EFIA reverse

<400> SEQUENCE: 20
agttccagta atcatgttct taatgaagtc                               30

<210> SEQ ID NO 21
<211> LENGTH: 546
<212> TYPE: DNA
<213> ORGANISM: Tulipa sp.
<220> FEATURE:
<221> NAME/KEY: CDS
<222> LOCATION: (49)..(168)
<220> FEATURE:
<221> NAME/KEY: CDS
<222> LOCATION: (258)..(434)

<400> SEQUENCE: 21

```
gatcatccag ttactaagct aagcaagccc tccttcctca acttatca atg act tca    57
                                                    Met Thr Ser
                                                     1 tcc acc tcc atc ctg aca tcc ctt gtg ctt ctc ttc ctc ctt gtc ggt   105
Ser Thr Ser Ile Leu Thr Ser Leu Val Leu Leu Phe Leu Leu Val Gly
  5                  10                  15 ctc gtc gag ccc cgc ctg gag att gaa ccc gga aac ggg ata gaa agg   153
Leu Val Glu Pro Arg Leu Glu Ile Glu Pro Gly Asn Gly Ile Glu Arg
 20                  25                  30                  35 tct ctt cta ggt ggg ctaagtaagc aactcttccg aactatcact aatcagtatg   208
Ser Leu Leu Gly Gly
                40 ttggtattct tagagagaag ttaaccatag attgttatga tgatcaggc tgc ggt gcg  266
                                                    Cys Gly Ala gcg tgc ttg gtg agg tgc agc gag tca tca agg ccg aat ctg tgc aag   314
Ala Cys Leu Val Arg Cys Ser Glu Ser Ser Arg Pro Asn Leu Cys Lys
 45                  50                  55
```

```
agg gcg tgc ggg aca tgc tgt gca agg tgc agc tgc gtc cca ccg ggc    362
Arg Ala Cys Gly Thr Cys Cys Ala Arg Cys Ser Cys Val Pro Pro Gly
 60              65                  70                  75 acc tac ggc aac tat gat agc tgc cct tgt tac gct tca ctc acc acc    410
Thr Tyr Gly Asn Tyr Asp Ser Cys Pro Cys Tyr Ala Ser Leu Thr Thr
                 80                  85                  90 cat cat ggt gct cgc aag tgc cct taaacatgaa gaataaattg gtgtgtcata   464
His His Gly Ala Arg Lys Cys Pro
             95 ggtgatgaaa gtgggttcgc ttgttcgata tatatatg taataaaacg ttcaaacaaa    524 ctcagttatt cgaataaaga gg                                            546

<210> SEQ ID NO 22
<211> LENGTH: 99
<212> TYPE: PRT
<213> ORGANISM: Tulipa sp.

<400> SEQUENCE: 22

Met Thr Ser Ser Thr Ser Ile Leu Thr Ser Leu Val Leu Leu Phe Leu
 1               5                  10                  15

Leu Val Gly Leu Val Glu Pro Arg Leu Glu Ile Glu Pro Gly Asn Gly
             20                  25                  30

Ile Glu Arg Ser Leu Leu Gly Gly Cys Gly Ala Ala Cys Leu Val Arg
         35                  40                  45

Cys Ser Glu Ser Ser Arg Pro Asn Leu Cys Lys Arg Ala Cys Gly Thr
     50                  55                  60

Cys Cys Ala Arg Cys Ser Cys Val Pro Pro Gly Thr Tyr Gly Asn Tyr
 65                  70                  75                  80

Asp Ser Cys Pro Cys Tyr Ala Ser Leu Thr Thr His His Gly Ala Arg
                 85                  90                  95

Lys Cys Pro

<210> SEQ ID NO 23
<211> LENGTH: 23
<212> TYPE: DNA
<213> ORGANISM: Artificial
<220> FEATURE:
<223> OTHER INFORMATION: primer GDSL-motif lipase forward

<400> SEQUENCE: 23
aggatttgag aacaccaatt tgc                                           23

<210> SEQ ID NO 24
<211> LENGTH: 27
<212> TYPE: DNA
<213> ORGANISM: Artificial
<220> FEATURE:
<223> OTHER INFORMATION: primer GDSL-motif lipase reverse

<400> SEQUENCE: 24
gagttcaatg acaagctgaa taagttg                                       27

<210> SEQ ID NO 25
<211> LENGTH: 22
<212> TYPE: DNA
<213> ORGANISM: Artificial
<220> FEATURE:
<223> OTHER INFORMATION: primer EF1a forward

<400> SEQUENCE: 25
tggtgtcaag cagatgattt gc                                            22
```

<210> SEQ ID NO 26
<211> LENGTH: 22
<212> TYPE: DNA
<213> ORGANISM: Artificial
<220> FEATURE:
<223> OTHER INFORMATION: primer EF1a reverse

<400> SEQUENCE: 26
ttcatcgtac cttgcctttg ag                                                  22

<210> SEQ ID NO 27
<211> LENGTH: 800
<212> TYPE: DNA
<213> ORGANISM: Rosa sp.
<220> FEATURE:
<221> NAME/KEY: CDS
<222> LOCATION: (1)..(540)

<400> SEQUENCE: 27

| cca | cat | ttc | cac | cat | cag | gcc | gat | cat | ccc | caa | tac | act | acc | tcc | caa | 48 |
| Pro | His | Phe | His | His | Gln | Ala | Asp | His | Pro | Gln | Tyr | Thr | Thr | Ser | Gln | |
| 1 | | | | 5 | | | | | 10 | | | | | 15 | | |

| tac | caa | gac | ttt | ctc | atc | gga | atc | gca | gcg | aat | ttc | gtg | aag | gaa | ctc | 96 |
| Tyr | Gln | Asp | Phe | Leu | Ile | Gly | Ile | Ala | Ala | Asn | Phe | Val | Lys | Glu | Leu | |
| | | | | 20 | | | | | 25 | | | | | 30 | | |

| tac | aag | ctc | gga | gct | cgg | aaa | att | tcc | gtg | gga | gga | ctg | cct | cca | atg | 144 |
| Tyr | Lys | Leu | Gly | Ala | Arg | Lys | Ile | Ser | Val | Gly | Gly | Leu | Pro | Pro | Met | |
| | | 35 | | | | | 40 | | | | | 45 | | | | |

| gga | tgc | ttg | cca | tta | gag | aga | acc | agt | aat | atc | atg | gat | gga | aat | gac | 192 |
| Gly | Cys | Leu | Pro | Leu | Glu | Arg | Thr | Ser | Asn | Ile | Met | Asp | Gly | Asn | Asp | |
| 50 | | | | | 55 | | | | | 60 | | | | | | |

| tgc | att | tcg | aat | tac | aac | gat | gtg | gct | ttg | gag | ttc | aat | gac | aag | ctg | 240 |
| Cys | Ile | Ser | Asn | Tyr | Asn | Asp | Val | Ala | Leu | Glu | Phe | Asn | Asp | Lys | Leu | |
| 65 | | | | 70 | | | | | 75 | | | | | 80 | | |

| aat | aag | ttg | acc | gtc | agc | ctc | aat | aaa | gag | ctt | cct | gga | agc | aaa | ttg | 288 |
| Asn | Lys | Leu | Thr | Val | Ser | Leu | Asn | Lys | Glu | Leu | Pro | Gly | Ser | Lys | Leu | |
| | | | | 85 | | | | | 90 | | | | | 95 | | |

| gtg | ttc | tca | aat | cct | tat | ttt | gtt | ttc | ctg | tat | atg | ata | aga | agg | cct | 336 |
| Val | Phe | Ser | Asn | Pro | Tyr | Phe | Val | Phe | Leu | Tyr | Met | Ile | Arg | Arg | Pro | |
| | | | 100 | | | | | 105 | | | | | 110 | | | |

| tct | ttt | tac | ggt | ttt | gag | gtg | aca | tca | gtg | gct | tgt | tgt | gcc | aca | gga | 384 |
| Ser | Phe | Tyr | Gly | Phe | Glu | Val | Thr | Ser | Val | Ala | Cys | Cys | Ala | Thr | Gly | |
| | | 115 | | | | | 120 | | | | | 125 | | | | |

| atg | ttt | gag | atg | gga | tat | gca | tgc | aac | cga | aac | aac | atg | ttc | aca | tgc | 432 |
| Met | Phe | Glu | Met | Gly | Tyr | Ala | Cys | Asn | Arg | Asn | Asn | Met | Phe | Thr | Cys | |
| 130 | | | | | 135 | | | | | 140 | | | | | | |

| act | gat | gca | agc | aaa | tac | atc | ttc | tgg | gac | tcc | ttc | cat | ccc | aca | gag | 480 |
| Thr | Asp | Ala | Ser | Lys | Tyr | Ile | Phe | Trp | Asp | Ser | Phe | His | Pro | Thr | Glu | |
| 145 | | | | 150 | | | | | 155 | | | | | 160 | | |

| aaa | gca | aac | cag | atc | atc | tct | gat | tac | ata | gtc | aaa | cgt | gtc | ctg | acc | 528 |
| Lys | Ala | Asn | Gln | Ile | Ile | Ser | Asp | Tyr | Ile | Val | Lys | Arg | Val | Leu | Thr | |
| | | | 165 | | | | | 170 | | | | | 175 | | | |

| cag | ttt | cct | taa | ttttccttca attaatatat gaaagctagg gcataaaatt | 580 |
| Gln | Phe | Pro | | | | attataaatc taggttccta tcactttaga taggttgata tatggcttta tccccagcta      640 ctatatttgt ttgtgcccaa ctaagtatag ttattactta ttaggttgtt tagaattgca      700 ttctggaggt aagtcttcat tttgcttttct acagtggatg tttctacttc caccatggag    760 tggcaatatg ataatacggt atttagtagt attgtagtac                            800

-continued

```
<210> SEQ ID NO 28
<211> LENGTH: 179
<212> TYPE: PRT
<213> ORGANISM: Rosa sp.

<400> SEQUENCE: 28

Pro His Phe His His Gln Ala Asp His Pro Gln Tyr Thr Thr Ser Gln
1               5                   10                  15

Tyr Gln Asp Phe Leu Ile Gly Ile Ala Ala Asn Phe Val Lys Glu Leu
            20                  25                  30

Tyr Lys Leu Gly Ala Arg Lys Ile Ser Val Gly Gly Leu Pro Pro Met
        35                  40                  45

Gly Cys Leu Pro Leu Glu Arg Thr Ser Asn Ile Met Asp Gly Asn Asp
    50                  55                  60

Cys Ile Ser Asn Tyr Asn Asp Val Ala Leu Glu Phe Asn Asp Lys Leu
65                  70                  75                  80

Asn Lys Leu Thr Val Ser Leu Asn Lys Glu Leu Pro Gly Ser Lys Leu
                85                  90                  95

Val Phe Ser Asn Pro Tyr Phe Val Phe Leu Tyr Met Ile Arg Arg Pro
            100                 105                 110

Ser Phe Tyr Gly Phe Glu Val Thr Ser Val Ala Cys Cys Ala Thr Gly
        115                 120                 125

Met Phe Glu Met Gly Tyr Ala Cys Asn Arg Asn Asn Met Phe Thr Cys
    130                 135                 140

Thr Asp Ala Ser Lys Tyr Ile Phe Trp Asp Ser Phe His Pro Thr Glu
145                 150                 155                 160

Lys Ala Asn Gln Ile Ile Ser Asp Tyr Ile Val Lys Arg Val Leu Thr
                165                 170                 175

Gln Phe Pro
```